US009874564B2

(12) United States Patent
Weissleder et al.

(10) Patent No.: US 9,874,564 B2
(45) Date of Patent: Jan. 23, 2018

(54) DETECTION OF TARGETS USING MAGNETIC RESONANCE

(75) Inventors: Ralph Weissleder, Peabody, MA (US); Hakho Lee, Acton, MA (US); David Issadore, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 983 days.

(21) Appl. No.: 14/006,389

(22) PCT Filed: Mar. 21, 2012

(86) PCT No.: PCT/US2012/029912
§ 371 (c)(1),
(2), (4) Date: Jan. 22, 2014

(87) PCT Pub. No.: WO2012/129281
PCT Pub. Date: Sep. 27, 2012

(65) Prior Publication Data
US 2014/0011217 A1 Jan. 9, 2014

Related U.S. Application Data

(60) Provisional application No. 61/515,150, filed on Aug. 4, 2011, provisional application No. 61/515,065, filed
(Continued)

(51) Int. Cl.
*G01V 3/00* (2006.01)
*G01N 33/574* (2006.01)
*G01N 24/08* (2006.01)

(52) U.S. Cl.
CPC ......... *G01N 33/574* (2013.01); *G01N 24/088* (2013.01); *G01N 33/57484* (2013.01);
(Continued)

(58) Field of Classification Search
USPC .......................................................... 324/309
See application file for complete search history.

(56) References Cited

U.S. PATENT DOCUMENTS 4,110,681 A    8/1978   Hofer et al.
5,164,297 A   11/1992   Josephson et al.
(Continued)

FOREIGN PATENT DOCUMENTS

WO    WO 2007147018    12/2007
WO    WO 2008075342     6/2008
(Continued)

OTHER PUBLICATIONS

International Preliminary Report on Patentability dated Apr. 15, 2010 in international application No. PCT/US2008/011541, 8 pages.
(Continued)

*Primary Examiner* — Rodney Fuller
(74) *Attorney, Agent, or Firm* — Fish & Richardson P.C.

(57) ABSTRACT

A portable magnetic resonance system includes a permanent magnet, a nuclear magnetic resonance probe, and control electronics. The control electronics are configured to transmit to the probe a magnetic resonance excitation signal having an excitation frequency f, receive from the probe a magnetic resonance measurement signal, detect in the magnetic resonance measurement signal a magnetic resonance frequency f0, and automatically adjust the excitation frequency f until the difference between the excitation frequency and the magnetic resonance frequency is approximately equal to a target offset.

12 Claims, 13 Drawing Sheets

Related U.S. Application Data on Aug. 4, 2011, provisional application No. 61/466,135, filed on Mar. 22, 2011.

(52) U.S. Cl.
CPC ............... *G01N 2333/4725* (2013.01); *G01N 2333/485* (2013.01); *G01N 2333/70596* (2013.01); *G01N 2333/71* (2013.01)

(56) References Cited

U.S. PATENT DOCUMENTS

| | | | |
|---|---|---|---|
| 5,166,620 A | 11/1992 | Panosh | |
| 5,423,315 A * | 6/1995 | Margosian | A61B 5/055 324/309 |
| 6,069,534 A | 5/2000 | Kobayashi | |
| 6,365,362 B1 | 4/2002 | Terstappen et al. | |
| 7,198,920 B1 | 4/2007 | Cheever | |
| 8,836,334 B2 * | 9/2014 | Lee | G01N 24/08 324/318 |
| 8,948,841 B2 * | 2/2015 | Martel | A61B 5/055 324/307 |
| 2002/0036500 A1 * | 3/2002 | Uetake | G01R 33/54 324/309 |
| 2002/0149369 A1 | 10/2002 | Peck et al. | |
| 2003/0104499 A1 | 6/2003 | Pressman | |
| 2003/0175947 A1 | 9/2003 | Liu et al. | |
| 2004/0014236 A1 | 1/2004 | Albo et al. | |
| 2007/0116602 A1 | 5/2007 | Lee | |
| 2007/0152669 A1 | 7/2007 | Park et al. | |
| 2007/0296413 A1 * | 12/2007 | Park | B82Y 30/00 324/309 |
| 2008/0113350 A1 | 5/2008 | Terstappen | |
| 2008/0305048 A1 | 12/2008 | Josephson et al. | |
| 2009/0146658 A1 * | 6/2009 | McDowell | G01N 24/088 324/309 |
| 2009/0275057 A1 | 11/2009 | Linke et al. | |
| 2011/0091987 A1 | 4/2011 | Weissleder et al. | |
| 2014/0178901 A1 | 6/2014 | Weissleder et al. | |

FOREIGN PATENT DOCUMENTS

| | | |
|---|---|---|
| WO | 2009-026251 | 2/2009 |
| WO | WO 2009/045551 | 4/2009 |
| WO | WO 2012/129325 | 9/2012 |

OTHER PUBLICATIONS

International Search Report and Written Opinion dated Dec. 18, 2008 in international application No. PCT/US2008/011541.
International Preliminary Report on Patentability in International Application No. PCT/US2012/029912, dated Sep. 24, 2013, 6 pages.
International Search Report and Written Opinion dated Jul. 19, 2012 in international application No. PCT/US2012/029976, 7 pgs.
International Preliminary Report on Patentability in International Application No. PCT/US2012/029976, dated Oct. 3, 2013, 6 pages.
Barna et al., "Structure Elucidation of the Teicoplanin Antibodies," J. Am. Chem. Soc., 6:4895-4902 (1984).
Bu, et al., "A new masking technology for deep glass etching and its microfluidic application," Sensors and Actuators A, 115(2-3):476-482 (2004).
Cheng et al., "Nanotechnologies for biomolecular detection and medical diagnostics," Curr. Opin. Chem. Biol., 10:11-19 (2006).
Chin et al., "Lab-on-a-chip devices for global health: past studies and future opportunities," Lab Chip, 7:41-57 (2007).
Danieli et al., "Small magnets for portable NMR spectrometers," Angew. Chem., 49:4113-4135 (2010).
El-Ali, et al., "Cells on chips," Nature, 442:403-411 (2006).
Giljohann and Mirkin, "Drivers of biodiagnostic development," Nature, 462:461-464 (2009) (Author Manuscript).

Gillis et al., "On $T_2$-shortening by strongly magnetized spheres: a partial refocusing model," Magn. Reson. Med., 47:257-263 (2002).
Grimm et al., "Novel nanosensors for rapid analysis of telomerase activity," Cancer Research, 64:639-643 (2004).
Gueron, "Nuclear Relaxation in Macromolecules by Paramagnetic Ions: A Novel Mechanism," J. Magn. Reson., 19:58-66 (1975).
Haun et al., "Bioorthogonal chemistry amplifies nanoparticle binding and enhances the sensitivity of cell detection," Nat. Nanotechnol., 5:660-665 (2010) (Author Manuscript).
Haun et al., "Micro-NMR for Rapid Molecular Analysis of Human Tumor Samples," Sci. Transl. Med., 3:71ra16, 13 pages (2011).
Issadore et al., "Self-assembled magnetic filter for highly efficient immunomagnetic separation," Lab Chip, 11:147-51 (2010) (Author Manuscript).
Josephson et al., "High-efficiency intracellular magnetic labeling with novel superparamagnetic-Tat peptide conjugates," Bioconjugate Chem., 10:186-191 (1999).
Josephson et al., "Magnetic Nanosensors for the Detection of Oligonucleotide Sequences," Angew. Chem., 113:3304-3306 (2001).
Kalluri and Weinberg, "The basics of epithelial-mesenchymal transition," J. Clin. Invest., 119:1420-8 (2009).
Keeler et al., "Reducing the Global Burden of Tuberculosis: The Contribution of Improved Diagnostics," Nature, 444:49-57 (2006).
Lee et al., "Chip-NMR biosensor for detection and molecular analysis of cells," Nat. Med., 14:869-874 (2008) (Author Manuscript).
Lee et al., "Rapid detection and profiling of cancer cells in fine-needle aspirates," Proc. Natl. Acad. Sci. U.S.A., 106:12459-12464 (2009).
Lee et al., "Ultrasensitive detection of bacteria using core-shell nanoparticles and an NMR-filter system," Angew. Chem., 48:5657-5660 (2009) (Author Manuscript).
Lequin, "Enzyme immunoassay (EIA)/enzyme-linked immunosorbent assay (ELISA)," Clin. Chem., 51(12):2415-2418 (2005).
Liu and Wang, "Nanomedicine: Nanotechnology tackles tumours," Nat. Nanotechnol., 2:20-1 (2007).
Liu et al., "CMOS mini nuclear magnetic resonance system and its application to bimolecular sensing," IEEE ISSCC Digest Tech. Papers, 140-141 (2008).
Liu et al., "Passive mixing in a three-dimensional serpentine microchannel," 2000, J Microelectromechanical Systems, 9(2):190-197 (2000).
Melin and Quake, "Microfluidic large-scale integration: the evolution of design rules for biological automation," Annu. Rev. Biomol. Struct., 36:213-231 (2007).
Moresi et al., "Miniature permanent magnet for table-top NMR," Concepts in Magnetic Resonance Part B: Magnetic Resonance Engineering, 19B(1):35-43 (2003).
Perez et al., "Magnetic relaxation switches capable of sensing molecular interactions," Nat. Biotechnol., 20:816-820 (2002).
Rosenthal et al., "Biocompatible quantum dots for biological applications," Chem Biol., 18:10-24 (2011).
Spencer et al., "Non-genetic origins of cell-to-cell variability in TRAIL-induced apoptosis," Nature, 459:428-32 (2009) (Author Manuscript).
Sun et al., "CMOS RF Biosensor Utilizing Nuclear Magnetic Resonance," IEEE J. Solid-State Circuits, 44:1629-1643 (2009).
Tan et al., "Biomarker-driven early clinical trials in oncology: a paradigm shift in drug development," Cancer J., 15:406-20 (2009).
Taylor et al., "A systems approach to model metastatic progression," Cancer Res., 66:5537-9 (2006).
Thaxton et al., "Nanoparticle-based bio-barcode assay redefines "undetectable" PSA and biochemical recurrence after radical prostatectomy," PNAS, 106(44):18437-18442 (2009).
Trumbull, et al., "Integrating microfabricated fluidic systems and NMR spectroscopy," IEEE Trans Biomed Eng., 47(1):3-7 (2000).
Tsourkas et al., "Magnetic Relaxation Switch Immunosensors Detect Enantiomeric Impurities," Angew. Chem., 116:2449-2453 (2004).
Urdea et al., "Requirements for high impact diagnostics in the developing world," Nature, 444:73-79 (2006).

(56) References Cited

OTHER PUBLICATIONS

Wensink et al., "Measuring reaction kinetics in a lab-on-a-chip by microcoil NMR," Lab Chip, 5:280-284 (2005).
Xia, et al., "Chaotic micromixers using two-layer crossing channels to exhibit fast mixing at low Reynolds numbers," Lab. Chip, 5:748-755 (2005).
Yager et al., "Point-of-care diagnostics for global health," Annu. Rev. Biomed Eng., 10:107-144 (2008).
Zhao et al., "Differential conjugation of tat peptide to superparamagnetic nanoparticles and its effect on cellular uptake," Bioconjugate Chem., 13:840-844 (2002).
Piyathilake et al., "The Expression of Ep-CAM ( 17-1 A) in Squamous Cell Cancers of the Lung," Human Pathology, 2000, 31(4):482-487.
US Final Office Action in U.S. Appl. No. 12/681,303, dated Aug. 27, 2014, 9 pages.
US Final Office Action in U.S. Appl. No. 12/681,303, dated May 30, 2012, 9 pages.
US Non-Final Office Action in U.S. Appl. No. 12/681,303, dated Feb. 6, 2012, 8 pages.
US Non-Final Office Action in U.S. Appl. No. 12/681,303, dated May 13, 2014, 9 pages.
Zellweger et al., "Expression patterns of potential therapeutic tm•gets in prostate cancer," Int. J. Cancer, 2005, 113:619-628.
International Search Report and Written Opinion dated Oct. 30, 2012 in International Application No. PCT/US2012/029912, 9 pgs.
U.S. Appl. No. 14/005,986, filed Nov. 27, 2013, Weissleder et al.
U.S. Appl. No. 12/681,303, filed Dec. 9, 2010, Weissleder et al.

\* cited by examiner

DETECTION OF TARGETS USING MAGNETIC RESONANCE

CLAIM OF PRIORITY

This is a U.S. National Phase Application under 35 U.S.C. § 371 of International Patent Application No. PCT/US2012/029912, filed on Mar. 21, 2012, which application claims the benefit of U.S. Provisional Patent Application Ser. Nos. 61/466,135, filed on Mar. 22, 2011; 61/515,065, filed on Aug. 4, 2011; and 61/515,150, filed on Aug. 4, 2011. The entire contents of the foregoing are hereby incorporated by reference.

STATEMENT AS TO FEDERALLY SPONSORED RESEARCH

This invention was made with Government support under Grant Numbers SN268201, CA119349, EB004626 and CA079443 awarded by the National Institutes of Health. The Government has certain rights in the invention.

BACKGROUND

The rapid and accurate measurement of biomarkers in biological samples provides information to quantify chemical entities, to facilitate early disease detection, and to gain insights into biology at the systems level. One approach to detecting such biomarkers includes using diagnostic magnetic resonance (DMR) technology. DMR has been developed as a platform to quantitatively and rapidly detect molecular biomarkers in biological samples. Based on the principle of nuclear magnetic resonance (NMR), DMR measures the relaxation time (longitudinal $T_1$ or transverse $T_2$) of proton spin in samples under a static magnetic field, in which biological targets of interest are labeled with target-specific magnetic particles (e.g., nanoparticles). Samples that contain magnetic particle-labeled biological targets have shorter relaxation times, as the NMR signal decays faster in the time domain. However, in some cases, changes in environmental and system temperatures lead to fluctuations in the static magnetic field. Such magnetic field fluctuations induce measurement artifacts. Accordingly, measurements obtained in the absence of a controlled environment may not be reliable. Furthermore, efforts to control the environmental and system temperatures increase cost and size of DMR systems, such that they are not desirable for point-of-care use.

SUMMARY

The present disclosure is directed toward systems and methods for detecting targets using magnetic resonance. Fluid samples, which may contain one or more target analytes, are combined with magnetic particles that act as proximity sensors. The mixture is exposed to an RF excitation signal and magnetic field and produces a nuclear magnetic resonance signal in response. Variations in the frequency of the measured magnetic resonance signal are compensated by adjusting the frequency of the RF excitation signal.

In one aspect, the present disclosure describes a portable magnetic resonance system that includes a permanent magnet, a nuclear magnetic resonance probe, and control electronics. The control electronics are configured to transmit to the probe a magnetic resonance excitation signal having an excitation frequency f, receive from the probe a magnetic resonance measurement signal, detect in the magnetic resonance measurement signal a magnetic resonance frequency $f_0$, and automatically adjust the excitation frequency f until the difference between the excitation frequency and the magnetic resonance frequency is approximately equal to a predetermined offset.

In some implementations, the control electronics are further configured to measure at least one of a sample longitudinal relaxation time $T_1$ and a sample transverse relaxation time $T_2$ from the magnetic resonance measurement signal when the difference between the excitation frequency and the magnetic resonance frequency is approximately equal to the predetermined offset.

In some implementations, the control electronics are configured to detect the magnetic resonance frequency $f_0$ based on a spectral power of the magnetic resonance measurement signal.

In certain implementations, the nuclear magnetic resonance probe includes an encapsulating block and a microcoil embedded within the encapsulating block. The encapsulating block can include polydimethylsiloxane (PDMS). The encapsulating block can include a bore for receiving a sample container. The microcoil can surround the bore.

In some implementations, the permanent magnet includes an opening configured to receive the nuclear magnetic resonance probe. The opening can extend from a first side of the magnet through the magnet center to a second opposite side of the magnet In some implementations, the diagnostic system includes a microfluidic network configured to contain a sample fluid.

In some implementations, the magnetic resonance diagnostic system further includes a portable data processing device to communicate with the control electronics, in which the portable data processing device is operable to transmit one or more commands to the control electronics to initiate measurement of at least one of a sample longitudinal relaxation time $T_1$ or a sample transverse relaxation time $T_2$, receive from the control electronics data corresponding to the sample longitudinal relaxation time $T_1$ or the sample transverse relaxation time $T_2$, or both, and output the data to a display.

In another aspect, a method of determining the presence of a target analyte in a fluid sample includes obtaining a fluid sample, mixing with the fluid sample multiple magnetic particles, in which each magnetic particle is bound to one or more binding moieties that specifically bind to the target analyte, exposing the fluid sample to a radiofrequency (RF) excitation signal, in which the RF excitation signal has an excitation frequency f, receiving a magnetic resonance measurement signal having a magnetic resonance frequency $f_0$, automatically adjusting the excitation frequency f until the difference between the excitation frequency f and the magnetic resonance frequency $f_0$ is approximately equal to a predetermined offset, and measuring at least one of a sample longitudinal relaxation time $T_1$ and a sample transverse relaxation time $T_2$ from the magnetic resonance measurement signal when the difference between the excitation frequency and the magnetic resonance frequency is approximately equal to the predetermined offset. The target analyte is present in the fluid sample when at least one of the measured sample longitudinal relaxation time $T_1$ and measured sample transverse relaxation time $T_2$ is shorter than a corresponding reference relaxation time.

In some implementations, automatically adjusting the excitation frequency f includes detecting the magnetic resonance frequency $f_0$ of the magnetic resonance measurement signal. Detecting the magnetic resonance frequency $f_0$ can include measuring a spectral power of the magnetic resonance measurement signal, comparing a peak spectral power of the measured magnetic resonance measurement signal to a threshold spectral power, automatically adjusting the excitation frequency f by a first amount until the peak spectral power exceeds the threshold spectral power, and identifying the frequency at which the peak spectral power exceeds the threshold power as the detected magnetic resonance frequency $f_0$. In some implementations, the first amount can be approximately equal to 10 kHz. Automatically adjusting the excitation frequency can further include adjusting an offset between the excitation frequency f and the magnetic resonance frequency $f_0$ to be approximately equal to the predetermined offset, after identifying the frequency at which the peak spectral power exceeds the threshold power. For example, the adjustment can modify the offset to be within 0.01%, 0.1%, 1%, 2%, 5%, or 10% of the predetermined offset. In some implementations, the predetermined offset can be about 3 kHz.

In some implementations, determining whether the target analyte is present in the sample includes comparing the at least one of a sample longitudinal relaxation time $T_1$ or a sample transverse relaxation time $T_2$ with a corresponding reference longitudinal relaxation time $T_{1R}$ or reference transverse relaxation time $T_{2R}$, determining that the target analyte is present in the sample when the at least one of a sample longitudinal relaxation time $T_1$ or a sample transverse relaxation time $T_2$ is shorter than a corresponding reference longitudinal relaxation time $T_{1R}$ or reference transverse relaxation time $T_{2R}$, and determining that the target analyte is not present in the sample when the at least one of a sample longitudinal relaxation time $T_1$ or a sample transverse relaxation time $T_2$ is greater than or approximately equal to a corresponding reference longitudinal relaxation time $T_{1R}$ or reference transverse relaxation time $T_{2R}$.

This disclosure relates to detecting targets using nuclear magnetic resonance.

As used herein, "linked" means attached or bound by covalent bonds, non-covalent bonds, or other bonds, such as van der Waals forces.

As used herein, "specifically binds" means that one molecule, such as a binding moiety, e.g., an oligonucleotide or an antibody, binds preferentially to another molecule, such as a target molecule, e.g., a nucleic acid or a protein, in the presence of other molecules in a sample.

As used herein, a "microcoil" is a small device that can be fabricated, for example, by forming a solenoid coil around a capillary tube or by creating a planar coil on a semiconductor or a glass substrate using microfabrication techniques. Such microcoils, whose inner diameters typically range in size between 0.1-0.5 mm (depending on the average size of the sample volume), are capable of obtaining high-quality NMR spectra with small sample volumes (nl-μl).

As used herein, a "monolithic integrated circuit" is a miniaturized electronic circuit that is formed on the surface of a substrate (e.g., silicon, glass, metal, polymer, or combinations of such materials). In general, the term "monolithic" means that one or more components are manufactured on one substrate. Such an integrated circuit (IC) can be fabricated using various microfabrication techniques (e.g., photolithography, etching, or other techniques).

As used herein, a "transceiver" is a device that contains both a transmitter and a receiver.

As used herein, the term "real-time," in the context of operations performed by the DMR system, means without any intentional delay, taking into account the processing limitations of the DMR system.

As used herein, the term "automatic," in the context of operations performed by the DMR system, means without need for further external user input.

As used herein, the term "predetermined offset" means an offset that is determined, established or defined in advance.

The new DMR systems and methods described herein provide several advantages. For example, the DMR systems can be used as a portable analytical instrument that can reliably, sensitively, and rapidly identify a range of biomarkers in realistic, point-of-care environments. The DMR systems are capable of automatically tuning measurement settings for consistent NMR readout. The DMR systems provide an easy-to-use interface for data collection and sharing. The DMR systems offer sensitive and yet cost-effective diagnosis. In addition, the new DMR detection strategies described herein can overcome considerable technological barriers to transferring laboratory applications of DMR technology to the point-of-care. With such capabilities, the new DMR systems are an essential tool for personalized medicine that enables the early detection of malignancies and the monitoring of treatment efficacy. They can also offer rapid and accurate diagnosis for infectious disease in resource-limited settings, mitigating a huge burden in public health.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, the drawings, and the claims.

DETAILED DESCRIPTION

Figure 1A:
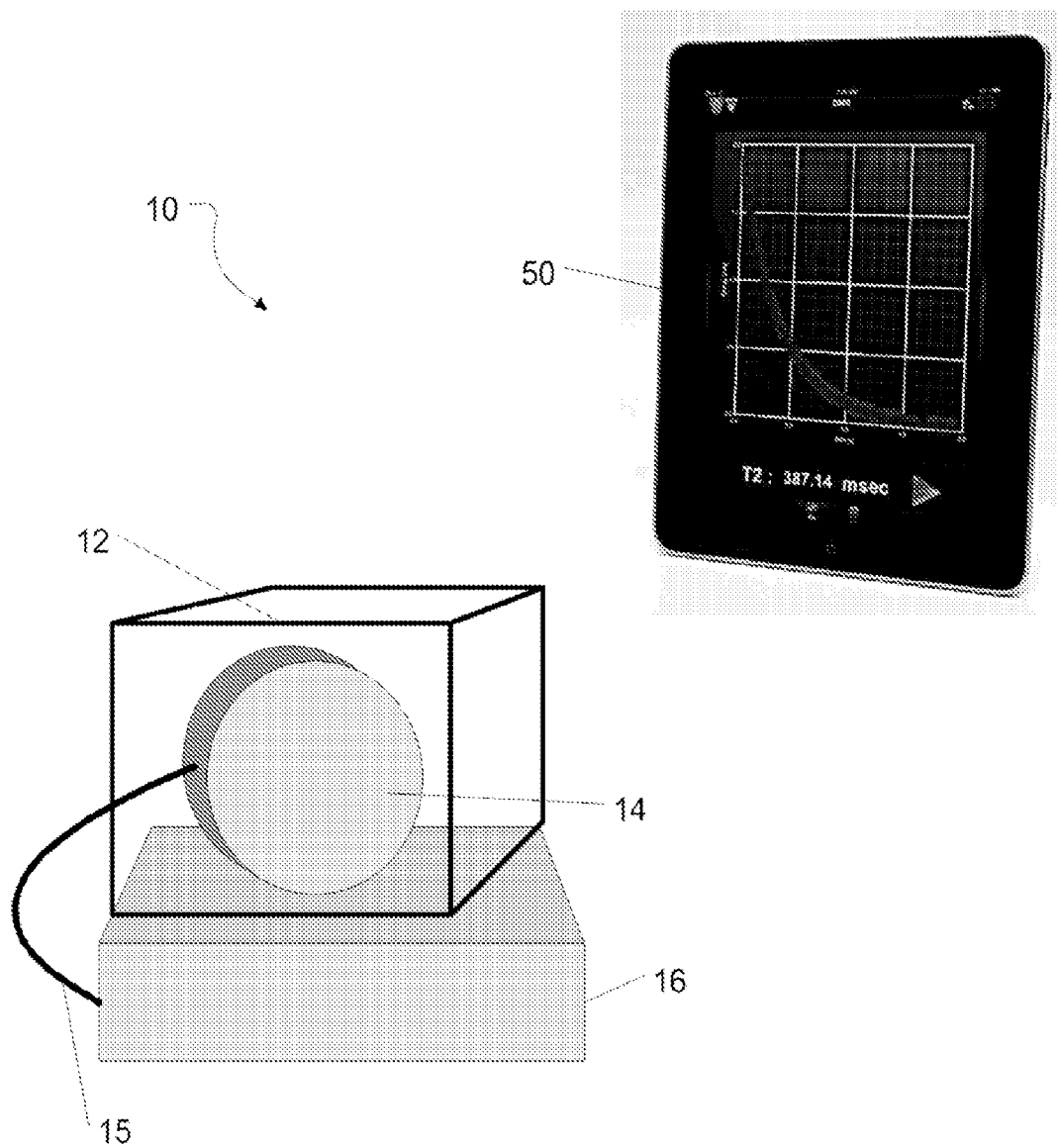
FIG. 1A is a schematic of an example of a diagnostic magnetic resonance (DMR) system.

The present disclosure is directed towards compact, programmable, and self-contained magnetic resonance systems for use in detecting various target molecules in samples (e.g., for diagnostic purposes). By adding samples and compositions that cause a specific interaction with target agents or analytes (e.g., a nucleic acid, a polypeptide, bacteria) within the sample, the systems can be used to provide rapid quantitative detection of biological targets. The systems include an electronic feedback system to automatically compensate for environmental variations, such as temperature-induced variations, in magnetic resonance, without the need for controlling of the device environment.

Diagnostic Magnetic Resonance System

In the presence of the static magnetic field, the nuclear spin of an atom or molecule will exhibit a small amount of polarization. When a radio frequency (RF) signal is applied over the static magnetic field at the proper frequency, the atom or molecule may transition from a low spin state to a higher spin state. When the RF signal is removed, the nuclear spin of the atom or molecule relaxes back to the lower spin state. This relaxation produces a measurable amount of RF signal at a resonant frequency, also known as the Larmor frequency $f_0$, associated with the transition. In a diagnostic magnetic resonance (DMR) system, a target agent or analyte (e.g., nucleic acid, bacteria, cells) in a sample is bound to magnetic particles (e.g., nanoparticles) to form a target-particle complex in a solution (e.g., a water based solution). The binding of the magnetic particles to the target analyte can, in some implementations, render the target-particle complex superparamagnetic. When both a static magnetic field and a pulsed RF signal having the proper frequency are applied to the complexes, the magnetic particles within the complexes produce local dipole fields with strong spatial dependence, which accelerates the spin relaxation of neighboring protons of the solution. Magnetically labeled complexes thus cause the nuclear magnetic resonance (NMR) signal produced by the neighboring protons to decay faster, leading to a shorter spin relaxation time, than the particles that are not bound to the target analytes.

The Larmor frequency $f_0$ of the detected NMR signal is proportional to the strength of the applied magnetic field B, i.e., $f_0=\gamma B/(2\pi)$, where $\gamma$ is the gyromagnetic constant. Accordingly, the frequency $f_0$ of the detected NMR signal will change when the magnitude of the static field changes. Typically, the magnetic field produced by a permanent magnet is temperature-dependent. For example, for an NdFeB magnet, a 1° C. increase in temperature causes the magnet's corresponding field strength to drop about 0.1% from its initial value, leading to an equivalent reduction in the frequency $f_0$. Such changes in frequency can distort measured signals and, in some implementations, lead to artifacts in the measured NMR signal. One approach for correcting the temperature-dependent change in Larmor frequency $f_0$ is to attempt to control environmental and system temperatures. However, controlling temperature can require large and expensive equipment, making a DMR system less practical for point-of-care applications (e.g., bedside patient analysis). Other environmental perturbations also can affect the magnitude of the Larmor frequency, including inadvertent movements of either the coil emitting the RF signal or permanent magnet with respect to one another.

FIG. 1A is a schematic of an example DMR system 10 that compensates for fluctuations in Larmor frequency without the need for controlling environmental changes (e.g., temperature changes, movement of coil position relative to permanent magnet). The system 10 includes a housing 12, a magnet assembly 14 within the housing 12, and corresponding control electronics contained within a separate enclosure 16. The housing 12 can be formed from any suitable material including, for example, glass, metal, or plastic (e.g., polymethylmethacrylate). Preferably, the housing 12 is formed from a material that is thermally insulating to reduce the effects of temperature variations on the magnet. The housing 12 is large enough to contain the magnet assembly 14 within the housing walls. For example, the housing can be about 3 in. deep by 5 in. wide by 4.5 in. tall. The enclosure 16 preferably sits next to or is fixed to the housing 12. The control electronics within the enclosure provide the NMR pulse sequences, collect the magnetic resonance signal from the sample, and communicate with external terminals.

The assembly 14 can be electronically coupled to the control electronics using, for example, a cable 15. Cable 15 can include any suitable cable-assembly for RF communication (e.g., SMA, SMB, BNC).

In some implementations, the DMR system 10 can include a portable data processing device 50 that can be coupled to the electronics contained in enclosure 16. For example, the portable data processing device 50 can include a cell phone, a portable electronic touch-screen device (e.g., an iPad®, iPod®), a laptop computer, or other portable electronic device. The device 50 can be configured to transmit one or more commands to the control electronics of the DMR system 12 to initiate NMR measurements. The device 50 also can be configured to receive from the control electronics any data measured by the DMR system 10 and transmit the measured data to a display. In some implementations, the device 50 can include software to arrange, analyze, and plot the data received from the control electronics. The portable device 50 can communicate with the DMR system through a wired-connection. For example, the connection method can include, but is not limited to a universal serial bus cable, optical fiber cable, or a coaxial cable. Alternatively, the assembly 10 can communicate with the portable device 50 wirelessly using any suitable communication method including, for example, WiFi connection, infrared connection, Bluetooth® connection.

Figure 1B:
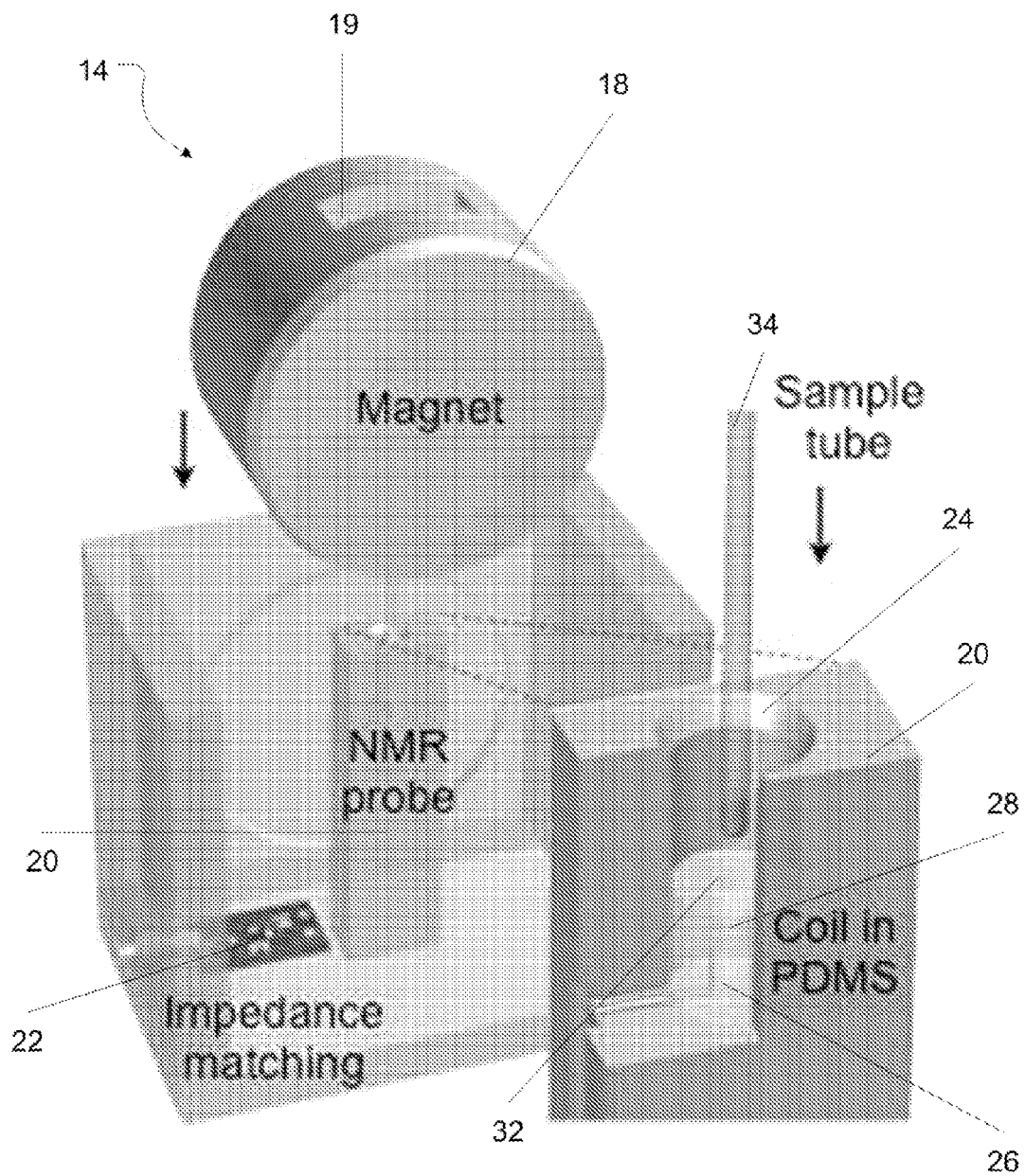
FIG. 1B is a schematic of an example of a magnet assembly of the DMR system of FIG. 1A.

FIG. 1B is a schematic of an example of a magnet assembly 14 arrangement inside the housing 12. The magnet assembly 14 includes a permanent magnet 18, an NMR probe 20 that includes a microcoil 28 and an impedance matching network 22. The magnet 18, microcoil 28, and matching network 22 are used to excite and read a nuclear magnetic resonance signal. The magnet 18 can be any suitable permanent magnet (e.g., NdFeB, SmCo) for providing a static polarizing magnetic field (e.g., about 0.001 T, 0.1 T, 0.3 T, 0.5 T, 1.5 T). The magnet shown in FIG. 2 has a cylindrical shape (e.g., 80 mm diameter by 39 mm tall), although other magnet shapes can be used as well. Preferably, the magnet shape is designed to maximize the homogeneity of the magnetic field. The magnet 18 includes an opening 19 for receiving the NMR probe 20. The NMR probe 20 is the portion of the system 10 used to transmit the RF excitation signal to the sample target and to receive the NMR signal produced by the sample in response to the RF excitation signal. The dimensions of the cross-sectional area of the opening 19 can be about 32 mm long by 14 mm wide, although other sizes are also possible. The opening 19 extends from a first side of the magnet 18 through the magnet center to a second opposite side of the magnet 18 so that the magnet 18 can be placed over and surround the probe 20.

Figure 1C:
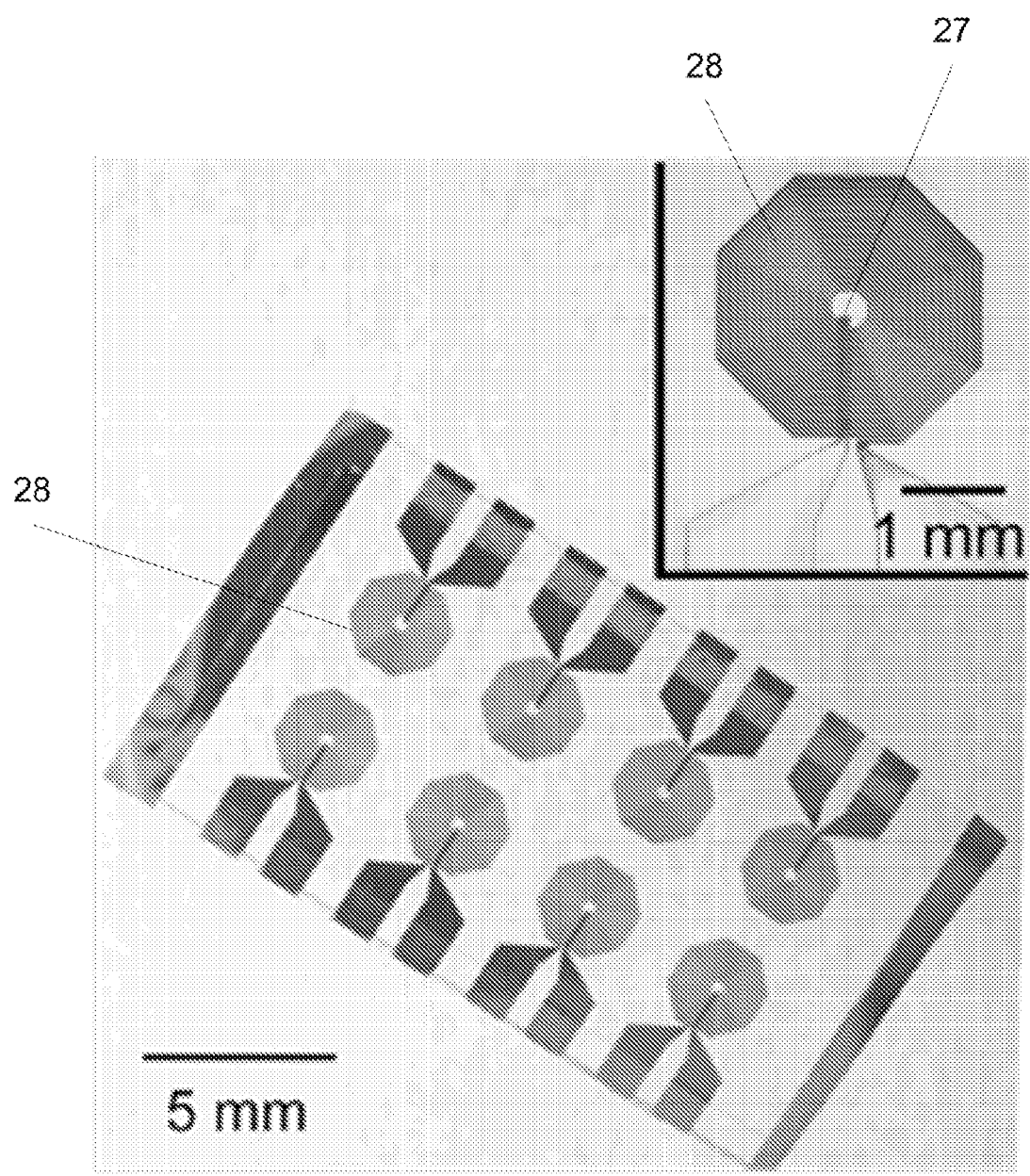
FIG. 1C is a photograph of an exemplary microcoil array.

FIG. 1B also shows an enlarged view of the NMR probe 20 in which the probe 20 is partially cut-away. The probe 20 includes a cavity 24 in which a microcoil assembly 26 is placed, thus encasing the assembly 26. The walls of the probe 20 that surround the assembly 26 can be formed of any suitable protective material including, for example, polymethyl metacrylate. The microcoil assembly 26 includes one or more microcoils 28 (e.g., 2, 4, 6, 8, or more microcoils) embedded within an insulating material (e.g., polydimethylsiloxane (PDMS)). FIG. 1C is a photograph of an exemplary microcoil array. The inset of FIG. 1C shows a single microcoil 28. The center of the coil 28 includes an open area/bore 32 for receiving sample to be tested/analyzed or for receiving a container holding the sample. In some implementations, the microcoil assembly 26 can be designed to increase the signal-to-noise ratio of the DMR measurement. For example, the coil 28 can be encased in PDMS, except for the bore 32 defined by the inner diameter of the coil. By encasing the coil 28 in PDMS, the bore 32 can be filled directly with the test sample, thus maximizing the signal produced by the sample. Alternatively, if a tube containing the sample was located in the bore 32, then the volume of material that would be analyzed is equivalent to the tube subtracted from the volume of the coil 28, thus reducing the overall signal produced. When using a sample container, samples are loaded into a thin-wall (e.g., 25 μm) tube 34, such as a polyimide tube, which is then introduced into the bore 32 for NMR detection. The microcoils 28 can be designed to have different center bore sizes based on the sample tube volumes used. For example, the microcoils can be designed to accommodate sample tubes having volumes ranging from 1 μl to 100 μl.

Although the DMR system 10 shows a sample tube being used to hold the target molecule and magnetic particles, any sample container can be used that places the sample in close enough proximity to be exposed to the magnetic field and RF signal of the DMR system. For example, the DMR system 10 can include a microfluidic network (not shown) for holding the samples to be analyzed. In particular, the microfluidic network can include one or more micro fluidic channels that are configured and arranged to manipulate (e.g., merge, mix, split, heat, and/or cool, among other operations) a fluid sample. For example, a microfluidic network as described in paragraphs eighty-one to eighty-eight of U.S. Patent App. Publication No. 2011/0091987, incorporated by reference herein in its entirety, can be used.

During operation of the system 10, a sample that may contain the target analyte is loaded into the sample tube 34 with magnetic particles that include a binding agent that specifically binds to the target analyte. A few or more magnetic particles may bind to their intended target and form "target analyte-particle complexes." Alternatively, or in addition, a collection of a plurality of target analyte-particle complexes are stuck/joined/bound together to form a "cluster" of complexes. The sample can include, for example, turbid samples such as blood, sputum, urine, or samples that have been prepared using techniques including, but not limited to, filtering or centrifugation. The sample tube 34 is placed in the bore 32 of the microcoil assembly 26 and exposed to a static magnetic field from the magnet 18. The control electronics are activated to generate a pulsed RF signal that is passed to the microcoil 28. Upon receiving the RF signal, the microcoil 28 is excited and wirelessly transmits the RF signal to the sample. The sensor can be tuned to operate at a frequency that energizes the magnetic particles (e.g., about 21.3 MHz). In response, the magnetic particles produce local dipole fields that accelerate the spin relaxation of neighboring protons in the sample (e.g., water protons). In some implementations, the target analyte-particle complexes and/or the clusters cause a substantial measurable decrease in the bulk spin relaxation time of surrounding water molecules. The water protons generate a magnetic resonance signal having a magnetic resonance frequency $f_0$, during the off-state of the pulsed RF signal. The magnetic resonance signal is received by the microcoil 28 and sent to the control electronics, where it is analyzed to determine the presence of the target analytes.

NMR Electronics

The control electronics of the DMR system are configured to transmit to the NMR probe 20 a magnetic resonance excitation signal having an excitation frequency f, receive from the probe a magnetic resonance measurement signal, detect in the magnetic resonance measurement signal a magnetic resonance frequency $f_0$, and automatically adjust the excitation frequency f until the difference between the excitation frequency and the magnetic resonance frequency is approximately equal to a predetermined offset.

In some embodiments, the control electronics for the DMR system are formed on a monolithic integrated circuit or "chip." In some embodiments, the control electronics are mounted on a printed circuit board to form a circuit board assembly in the enclosure 16. In some embodiments, some circuitry of the control electronics is formed on a chip and combined with other circuitry (e.g., impedance matching circuits, filtering circuits, acquisition circuits) that is off the chip. The printed circuit board can be fabricated by any suitable method known in the art (e.g., silk screen printing, photoengraving, PCB milling, electroplating). The circuit board can have a single layer or multiple layers.

Figure 2:
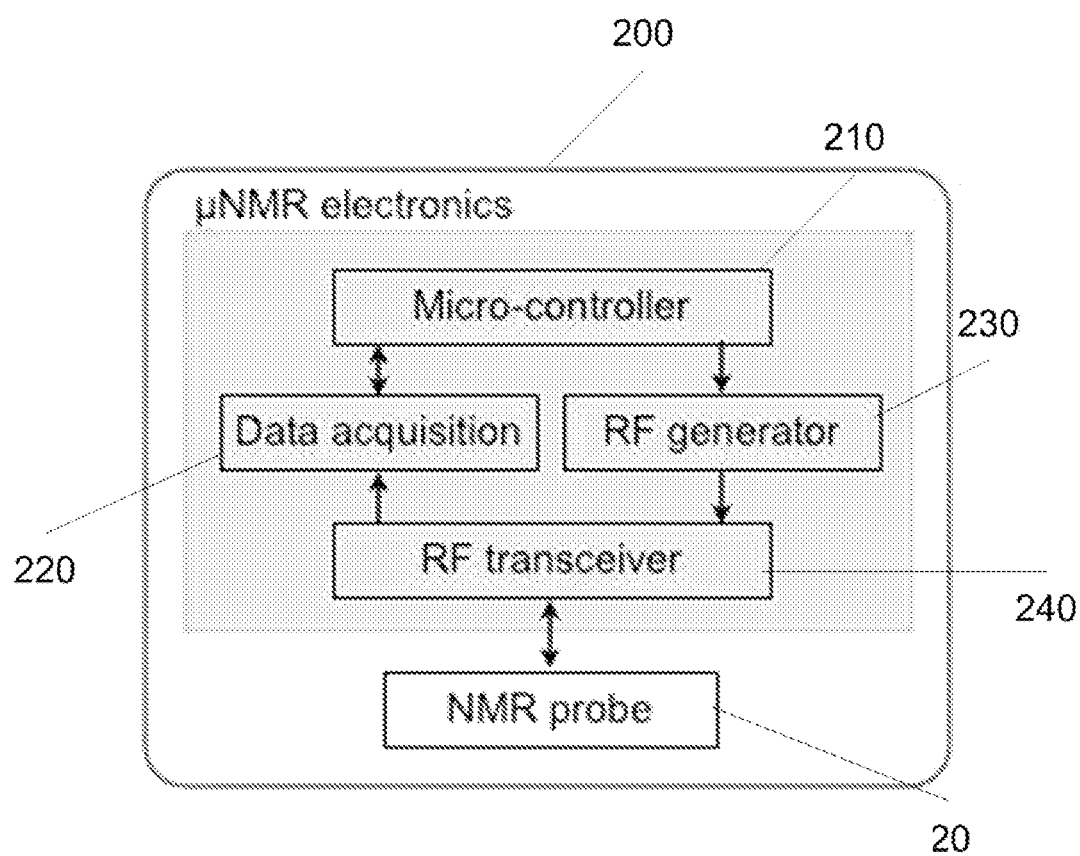
FIG. 2 is a diagram showing the control electronics for the DMR system.

FIG. 2 is a diagram showing the control electronics 200 for the DMR system. The control electronics 200 are coupled to the NMR probe 20 and include a microcontroller unit (MCU) 210, a data acquisition unit 220, a RF generator 230, and a RF transceiver 240. The MCU 210 orchestrates the operation of the other units of the control electronics, processes raw data, and communicates with an external data processing device for data transfer and user-control.

Architecture Design Consideration

Figure 3:
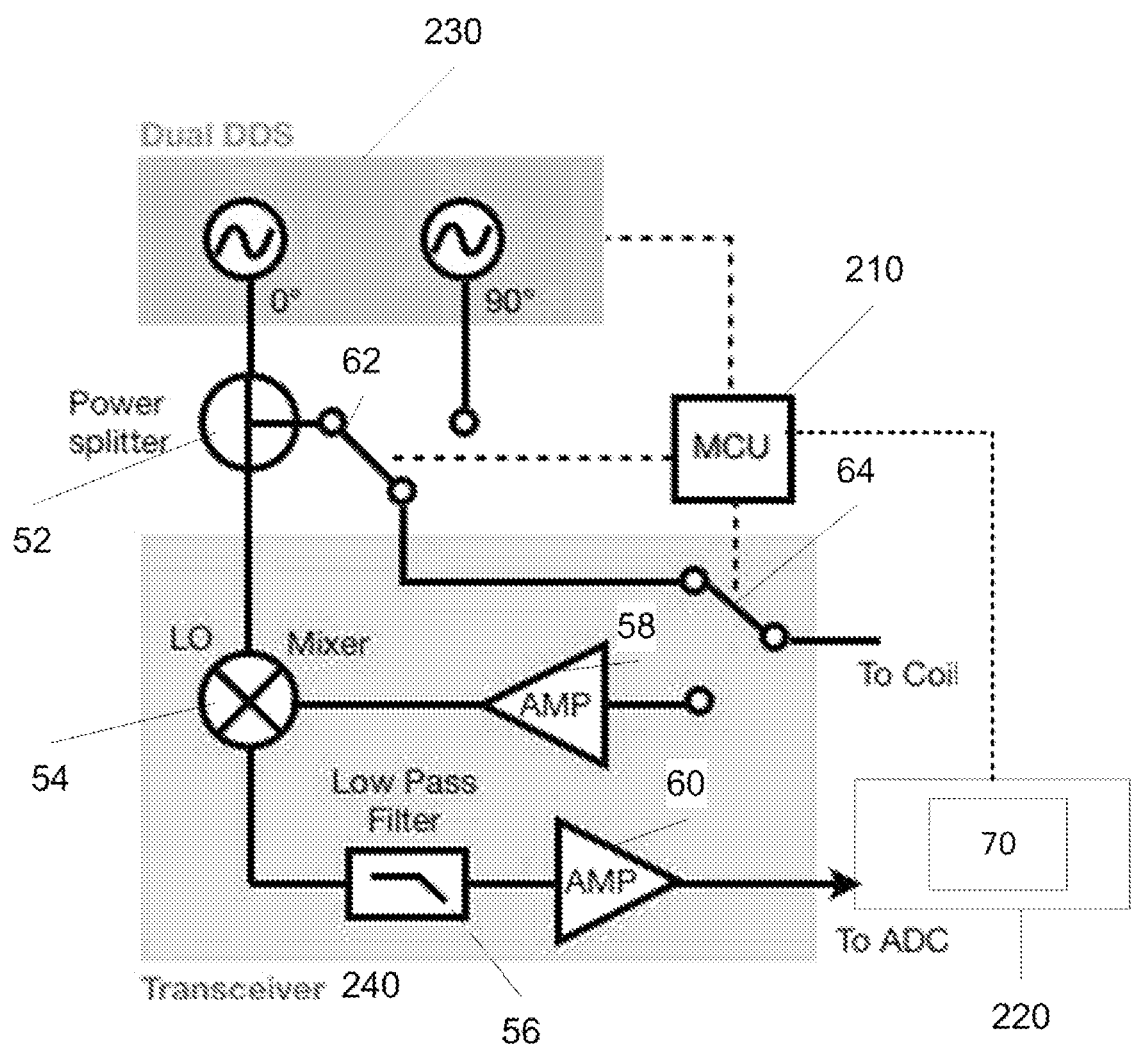
FIG. 3 is a schematic of part of a radio frequency (RF) transceiver of the control electronics of a DMR system.

FIG. 3 is a schematic of part of the RF transceiver 240 used to energize the microcoil 28. The transceiver 240 can be formed on a monolithic complementary metal oxide semiconductor (CMOS) integrated circuit integrated circuit (IC). The RF transceiver 240 contains various components (e.g., power splitter 52, mixer 54, low pass filter 56, low noise amplifiers 58, 60, and switches 62, 64). The IC can be fabricated, for example, using 0.18 μm CMOS processes. RF signals are received in the transceiver 240 from one or more direct digital synthesis (DDS) chips, which serve as the RF generator 230. These RF signals (S1 and S2) have a phase offset of 0° and 90°, respectively. In Carr-Purcell-Meiboom-Gill (CPMG) measurements (discussed further below in the section entitled, "Use of DMR Systems"), S1 is used to provide pulses having a π/2 phase offset, whereas S2 is used to provide pulses having a π phase offset. The signal generated by S1 is divided by power splitter 52 and provided to a local oscillator (LO) input of mixer 54. Pulse sequences are created by modulating the RF carrier signals using voltage-controlled switches 62, 64 that are gated by the MCU 210. The pulsed RF signals then are passed to the microcoil 28 of the NMR probe 20. In general, excitation frequencies range from between about 20 MHz to about 22 MHz, although any suitable excitation frequency in the range produced by the DDS chip can be used (e.g., up to about 160 MHz).

When a magnetic resonance signal is received by the coil 28 of the NMR probe 20, the resonance signal is amplified, e.g., by a low noise amplifier 58 and sent to the mixer 54 for frequency down-conversion from the MHz range to the audio range (e.g., from about 20 MHz to 1-10 kHz). The down-converted signal can be further conditioned by a low pass filter 56 and a second low noise amplifier 60. The signal then is sent to an analog-to-digital conversion component 70 of the data acquisition unit 220, which is electronically coupled to the MCU 210. (See, e.g., FIG. 2) The data is passed from the data acquisition unit 220 to the MCU, where the MCU 210 then processes the digital data to determine the magnetic resonance frequency $f_0$ and transfers the data to an external data processing device 50 (e.g., computer or mobile computing device; see FIG. 1A) using a communication channel (e.g., universal serial bus, WiFi connection, infrared connection, Bluetooth® connection, among others). The external data processing device can include a graphical interface for inputting commands and reviewing data received from the system.

In some implementations, a heterodyne transceiver architecture can be used, where the local oscillator frequency is set to be slightly offset (e.g., about 1 kHz) higher or lower than the NMR resonance signal frequency. As a result, the frequency of the excitation signal is also slightly off from the NMR resonance signal frequency. This architecture can significantly reduce high frequency noise and simplify the design of any off-chip low pass filters and data acquisition systems that are used. Although the signal frequency differs from the NMR resonance frequency, the signal frequency is still close enough to excite the spin of the magnetic particles. Alternatively, the excitation signal can be directly amplified at the NMR resonance frequency, or a homodyne transceiver can be used. Additional information about the control electronics can be found in U.S. Patent App. Publication No. 2011/0091987, e.g., paragraphs sixty-five to eighty.

Temperature Compensation

As explained above, the Larmor frequency $f_0$ of an NMR signal received by the microcoil can vary with fluctuations in the magnitude of the applied static magnetic field (provided by the permanent magnet), for example, due to temperature changes. Small changes in temperature (e.g., 1° C.) can induce significant changes in the Larmor frequency (e.g., 20 kHz or more). In some cases, the changes in frequency are so large that they cause the down-converted NMR signal to drift beyond the passband (e.g., less than 30 kHz) of the low-pass filter of the control electronics. As a result, the measured signal can be substantially attenuated, leading to artifacts in the measured NMR signal profile.

In some embodiments, the control electronics of the DMR system 10 are configured to track and compensate for such drifts in Larmor frequency. In particular, the MCU 210 and/or the RF generator 230 can be programmed to automatically execute a real-time tracking and compensation algorithm that adjusts the frequency f of the excitation signal transmitted by the microcoil. For example, in some embodiments, the system 10 is configured to identify the Larmor frequency $f_0$ of a measured NMR signal and, depending on the value of the identified frequency $f_0$, adjust an excitation frequency f of an RF signal applied to a sample. The system performs the tracking and compensation in real-time by measuring the Larmor frequency and adjusting the excitation signal frequency without any intentional delay, taking into account the processing limitations of the DMR system and the time required to accurately perform measurements and adjust frequencies. Once a user initiates operation of the system 10, the system 10 performs measurements and analysis without the need for further external user input, i.e., it automatically performs the measurements and analysis.

Microfluidics

In some embodiments, an optional microfluidic channel network can be used in place of the sample tube arrangement shown in FIG. 2. Microfluidic systems can be used in the DMR system 10 to facilitate control and manipulation (e.g., separation, segregation) of small volumes of liquid and help isolate targets from a complex parent specimen. During the sensing process, microfluidic elements provide vital functions, for example, handling of biological fluids, reproducible mixing of magnetic particles with samples, distribution of aliquots to different coils for parallel sensing, and confining of samples to the most sensitive region of a given microcoil. Additional information about microfluidic channel networks and their fabrication can be found in U.S. Patent App. Publication No. 2011/0091987, e.g., in paragraphs eighty-one to eighty-eight.

Microcoil

In some embodiments, a single solenoid microcoil is used to transmit the RF signal to a sample. Alternatively, array-based microcoils can be used in place of a single microcoil. A microcoil array can have a number of microcoils and allows multiple measurements to be carried out simultaneously. For example, as shown in FIG. 1D, the microcoil array can include eight microcoils arranged in a planar configuration (e.g., microcoils arranged along a single plane).

The microcoils can be formed from any suitable electrically conductive metal (e.g., copper) fabricated by any known method, such as complementary metal oxide semiconductor (CMOS) compatible microfabrication technology, deposition or growth techniques (e.g., thermal oxidation, sputtering, evaporative deposition, chemical vapor deposition, epitaxy, electroplating), patterning techniques (e.g., photolithography, shadow masking, focused-ion-beam milling, electron-beam lithography, microcontact printing), or etching techniques (e.g., plasma etching, chemical etching).

Solenoid microcoils, such as microcoil 28 in FIG. 1B, are constructed by wrapping a fine copper wire around a polyethylene tube and subsequently immersing the coil into a polymer (e.g., PDMS). Following polymer curing, the tube is retracted to create a bore (e.g., see bore 32 in FIG. 2)

capable of receiving a sample tube. In some embodiments, the microcoils can be fabricated on any suitable substrate, such as glass, ceramic, silicon, sapphire, polyimide film (e.g., Kapton®), Teflon®, or gallium arsenide. The microcoils can transmit RF signals to the sample (located, e.g., in a tube or microfluidic channel network) as well as receive NMR signals from the sample. In other embodiments, a microcoil can be used for transmitting RF excitation pulses whereas a separate microcoil can be used for detecting NMR signals. By the application of a DC current, the microcoils can also be used to environmentally heat samples and to concentrate magnetically labeled targets by forming magnetic traps. Additional information about the microcoil fabrication process and the types of microcoils that can be used in DMR measurement systems can be found in U.S. Patent App. Publication No. 2011/0091987, e.g., in paragraphs eighty-nine to ninety-two.

Use of Magnetic Particles

As noted above, a sample that may contain a target analyte is mixed with a liquid containing a number of particles that are designed to specifically bind to the target analyte. The particles can include magnetic particles (e.g., nanoparticles) that form a target-particle complex in solution.

Particles

Magnetic particles include one or more inner magnetic cores and an outer coating, e.g., a capping polymer. The magnetic cores can be monometallic (e.g., Fe, Ni, Co), bimetallic (e.g., FePt, SmCo, FePd, FeAu) or can be made of ferrites (e.g., $Fe_2O_3$, $Fe_3O_4$, $MnFe_2O_4$, $NiFe_2O_4$, $CoFe_2O_4$). The magnetic particles can be nanometers or micrometers in size, and can be diamagnetic, ferromagnetic, or superparamagnetic. The outer coating of a particle increases its water-solubility and stability and also provides sites for further surface treatment with binding moieties.

Binding Moieties

In general, a binding moiety is a molecule, synthetic or natural, that specifically binds or otherwise links to, e.g., covalently or non-covalently binds to or hybridizes with, a target molecule, or with another binding moiety (or, in certain embodiments, with an aggregation inducing molecule). For example, the binding moiety can be a synthetic oligonucleotide that hybridizes to a specific complementary nucleic acid target. The binding moiety can also be an antibody directed toward an antigen or any protein-protein interaction. Also, the binding moiety can be a polysaccharide that binds to a corresponding target. In certain embodiments, the binding moieties can be designed or selected to serve, when bound to another binding moiety, as substrates for a target molecule such as enzyme in solution. Binding moieties include, for example, oligonucleotide binding moieties, polypeptide binding moieties, antibody binding moieties, and polysaccharide binding moieties. As an example, streptavidin has four sites (binding moieties) per molecule that will be recognized by biotin.

Conjugate Preparation

The surface of the magnetic particles are treated to present functional groups (e.g., —$NH_2$, —COOH, —HS, —$C_nH_{2n-2}$) that can be used as linkers to subsequent attachments of other molecules (e.g., antibodies, drugs). In some cases, the surface treatment makes the magnetic particle essentially hydrophilic or hydrophobic. The surface treatment can be formed of polymers including, but not limited to, synthetic polymers such as polyethylene glycol or silane, natural polymers, derivatives of either synthetic or natural polymers, and combinations thereof.

In some implementations, the surface treatment is not a continuous film around the magnetic particle, but is a "mesh" or "cloud" of extended polymer chains attached to and surrounding the magnetic particle. Exemplary polymers include, but are not limited to polysaccharides and derivatives, such as dextran, pullanan, carboxydextran, carboxmethyl dextran, and/or reduced carboxymethyl dextran, polymethylmethacrylate polymers and polyvinyl alcohol polymers. In some implementations, these polymer coatings provide a surface to which targeting moieties and/or binding groups can bind much easier than to the shell material. For example, in some embodiments magnetic particles (e.g., iron oxide nanoparticles) are covered with a layer of 10 kDa dextran and then cross-linked with epichlorohydrin to stabilize the coating and form cross-linked magnetic particles.

Selectivity

By conjugating magnetic particles with binding moieties (e.g., biotin, monoclonal antibody) that will specifically bind to intended targets, a high selectivity can be achieved to enhance the accuracy of the DMR system assay.

Consider, for example, magnetic particles with surfaces coated with biotin (a vitamin) that specifically bind to avidin (a protein). If avidin exists in a sample, the coated magnetic particles suspended in the sample will self-assemble into clusters. The clustering can be sensed, and the presence of avidin inferred, because the clusters (as opposed to individual, unclustered particles) introduce greater local magnetic field modulations and therefore reduce T2 relaxation time. This detection scheme, which is referred to herein as a "magnetic relaxation switch," is a general sensing modality that can detect a variety of target biomolecules (e.g., proteins, bacteria, viruses, cancer markers) by using magnetic particles with surfaces modified with binding moieties that specifically bind to the target objects.

Use of DMR Systems

Operation of the DMR System

Figure 4:
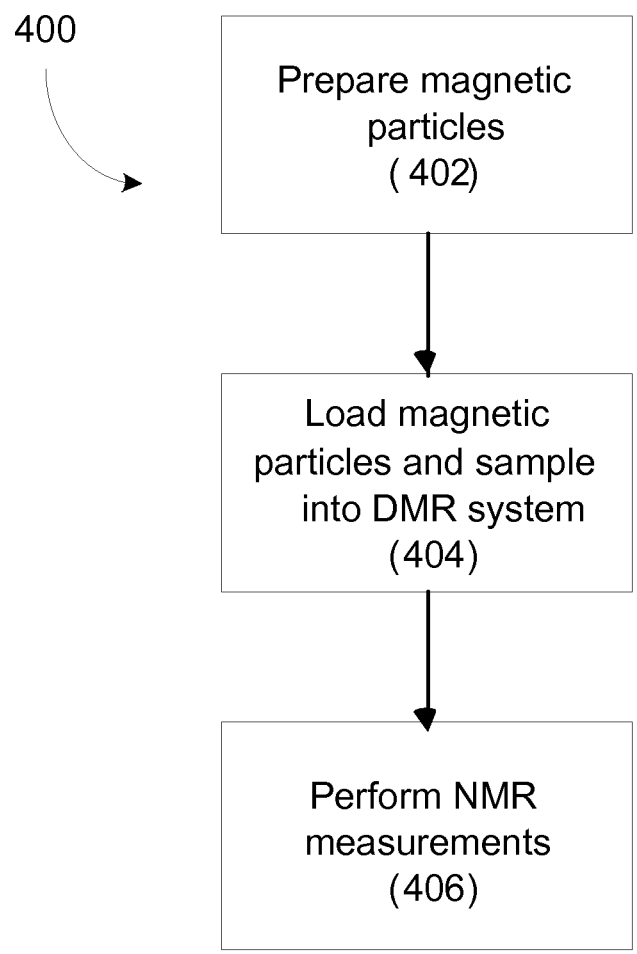
FIG. 4 is a flowchart describing a method for using a DMR system to perform measurements.

A flowchart 400 in FIG. 4 describes a series of steps for using the DMR system 10 to perform measurements. For example, in a first step 402, magnetic particles (e.g., cross-linked magnetic nanoparticles) that specifically bind to a desired target analyte are prepared. In a second step 404, the magnetic particles and the sample to be measured are combined in a solution and placed in a sample tube (e.g., sample tube 34), and the sample tube is then placed in the DMR system (e.g., in bore 32 of system 10). The sample can include, for example, turbid samples such as blood, sputum, urine, or samples that have been prepared using techniques including, but not limited to, filtering or centrifugation.

In some embodiments, where targeting of relatively large objects is desired (e.g., bacteria or mammalian cells), the target objects are first labeled with the magnetic particles and then unbound magnetic particles are removed from the sample prior to performing the measurements of the NMR signal. Alternatively, the sample and magnetic particles can be combined in a micro fluidic channel network of the DMR system. Typically when particles adhere to larger objects, such as cells, the particles are not in close enough proximity to cause a clustering effect on the T2 signal. Rather, as the particles coat the cell the dominant effect that is measured is an increase in the total number of particles in the sample volume.

Once the sample and magnetic particle solution is loaded into the DMR system, NMR measurements are performed in step 406. For example, the control electronics of the DMR system provide pulse sequences to measure a longitudinal relaxation time ($T_1$) and/or a transverse relaxation time ($T_2$). The $T_1$ of a sample can be measured using inversion recovery (IR) pulse sequences. The $T_2$ of a sample can be measured using Carr-Purcell-Meiboom-Gill (CPMG) spin echo pulse sequences. The pulse widths required to cause a 90° and a 180° rotation of nuclear spins are determined by generating nutation curves for each microcoil of the DMR system. Nutation means an oscillation of the axis of a rotating object; specifically, the periodic variation of the inclination of a spinning magnetic moment that experiences a torque from an external magnetic field.

Figure 5:
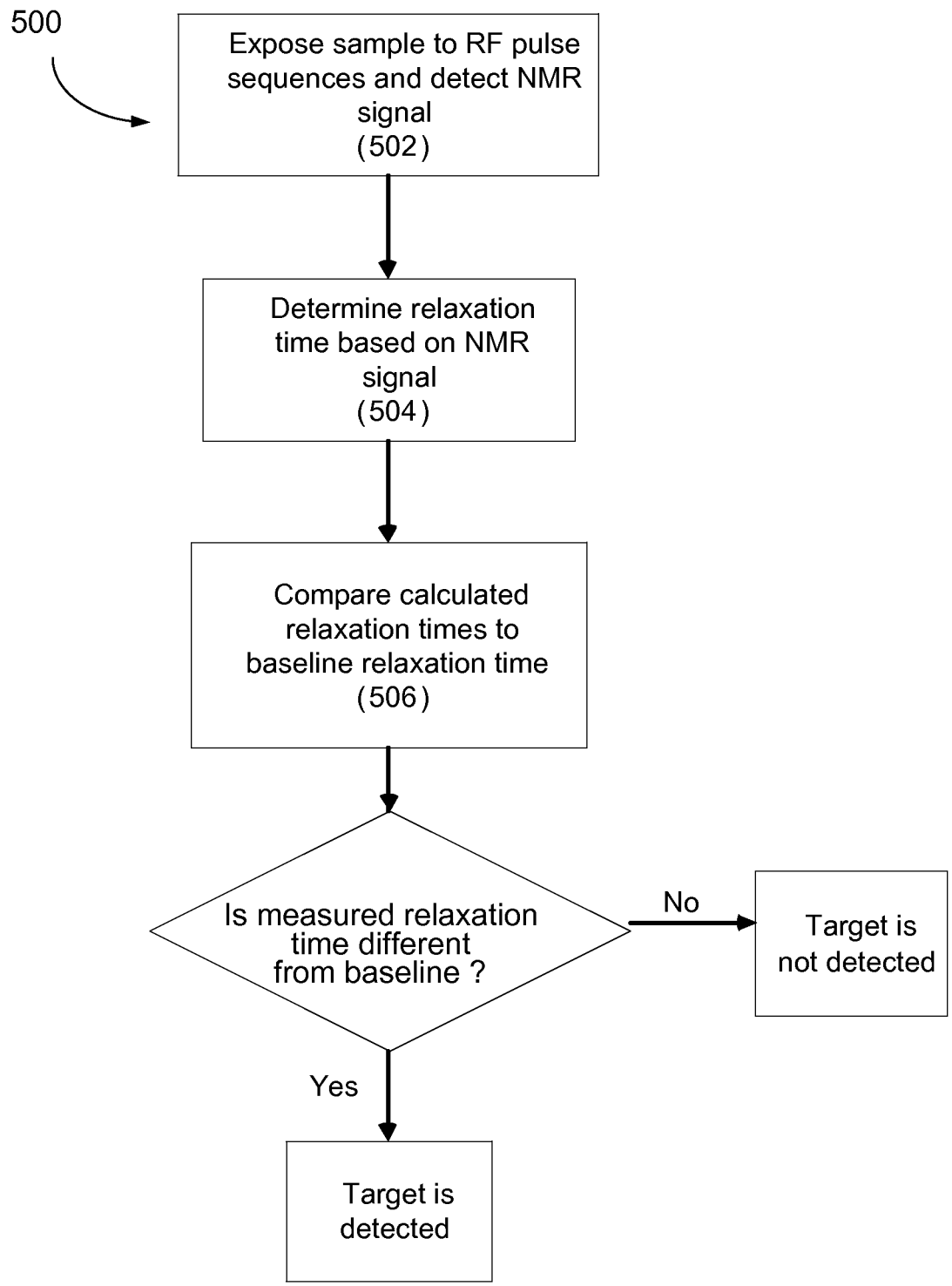
FIG. 5 is a flowchart describing a method for using a DMR system to determine whether or not a target is present in a sample.

A flowchart 500 in FIG. 5 describes a series of steps for using the DMR system 10 to determine whether or not a target is present in a sample. A sample mixture containing magnetic particles is exposed to RF pulse sequences and data is acquired using a DMR system (step 502). The relaxation time or times for each mixture (e.g., the combination of sample and magnetic particles) are determined (step 504) using the acquired data. The calculated relaxation time or times for each mixture is compared (step 506) to a baseline relaxation time or times of the magnetic particles that do not have attached targeting moieties. The baseline relaxation times can be measured directly or can be obtained from a reference. If the measured relaxation time or times of the mixture do not differ from the baseline time, this indicates that the target is not present in the sample (step 508). If the measured relaxation time or times of the mixture are sufficiently shorter than the baseline time (e.g., the difference is greater than the system noise level) then the target is present in the sample, and is considered to be "detected" (step 510). For example, in some implementations, the noise level of the DMR system is approximately 2%. Therefore, changes in measured relaxation time ($T_1$ or $T_2$) greater than 2% indicate the target is present. In general, as the signal to noise level increases, the concentration detection threshold is reduced by a proportional amount. Alternatively, with an increased signal to noise level, the same detection threshold can be maintained for a smaller sample volume.

For example, to detect avidin in solution, two samples are prepared: magnetic particles without targeting molecules (also referred to herein as "binding moieties" or "binding ligand") (e.g., CLIO—$NH_2$) and magnetic particles that are conjugated to targeting molecules (e.g., CLIO-biotin-avidin). First, a baseline measurement of $T_2$ is obtained for the CLIO—$NH_2$ particles. Next, a second measurement of $T_2$ is obtained for the CLIO-biotin-avidin particles. A difference in $T_2$, or $\Delta T_2$, is calculated by subtracting the second $T_2$ measurement from the baseline $T_2$ measurement.

Next, to produce a calibration curve for detection, a known amount of the target analyte (e.g., avidin) is added to samples in different concentrations and $\Delta T2$ is measured for each concentration, as described above. These experiments are then repeated with different concentrations of the target analyte to generate a calibration curve.

In alternative embodiments, a different method of calibration can be used that consists of measuring the inverse T2 (i.e., $R_2=1/T_2$) of three samples: a target sample (e.g., blood, serum), magnetic particles that have been conjugated to binding moieties, and magnetic particles that have not been conjugated to binding moieties. For example, a first sample containing just blood or serum is used to obtain a first baseline value ($R_{2w}=1/T_{2w}$). A second sample is then measured to account for non-specific binding of the magnetic particles to obtain a second baseline value ($R_{2\emptyset}$). The third sample is the test sample and is used to measure the test value $R_{2test}$. Calibration of the test value then is performed based on the following equation $R_2=(R_{2test}-R_{2w})/(R_{2\emptyset}-R_{2w})$. In alternative embodiments, the baseline $T_2$ can be a known, standard quantity (e.g., the relaxation rate or rates of blood free from pathogens or disease).

Temperature Compensation

Figure 6A:
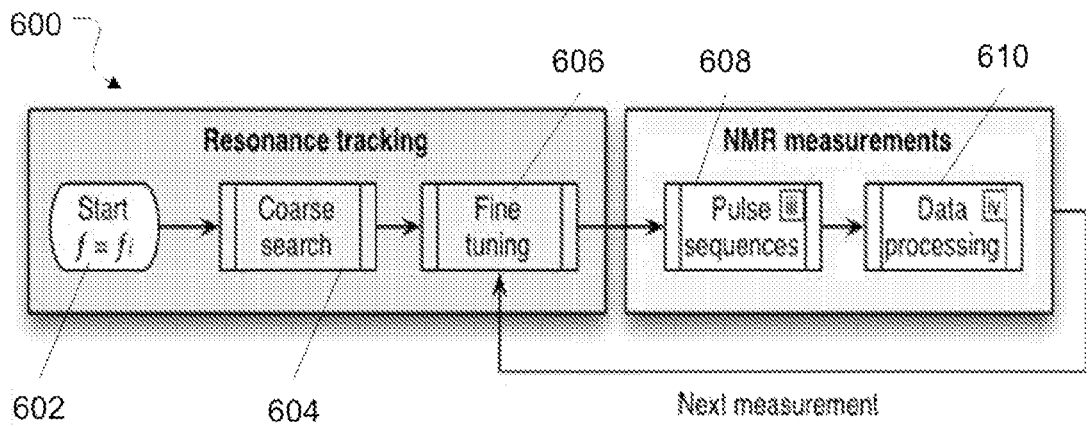
FIG. 6A is a flowchart describing a process implemented by a DMR system to compensate for temperature changes.

A flowchart 600 in FIG. 6A describes the process implemented by the DMR system 10 to compensate for temperature changes during measurements by monitoring the Larmor frequency $f_0$ of a measured NMR signal and automatically adjusting the RF frequency f of the excitation signal provided to the microcoil for sample excitation. For example, in a first step (602) the RF excitation frequency f is set equal to an initial excitation frequency $f_i$. Selection of the initial excitation frequency $f_i$ is based on the expected value of the Larmor frequency $f_0$. The initial frequency is chosen based on the nominal value (B0) of the magnetic field produced by the permanent magnet. The initial frequency $f_i$ is $f_i$=gB0, where gB0 is the gyromagnetic ratio for Hydrogen. In some implementations, the initial excitation frequency $f_i$ is set equal to a value that is offset from the expected Larmor frequency of the NMR signal to be measured (e.g., $f_i$ can be set equal to about 1 kHz, about 2 kHz, about 3 kHz, or more from the Larmor frequency). The predetermined offset can be established, defined or determined in advance of performing the measurement and compensation process. After the initial excitation frequency $f_i$, is set, the DMR system 10 performs a coarse search for the Larmor frequency $f_0$ in a second step (604).

Figure 6B:
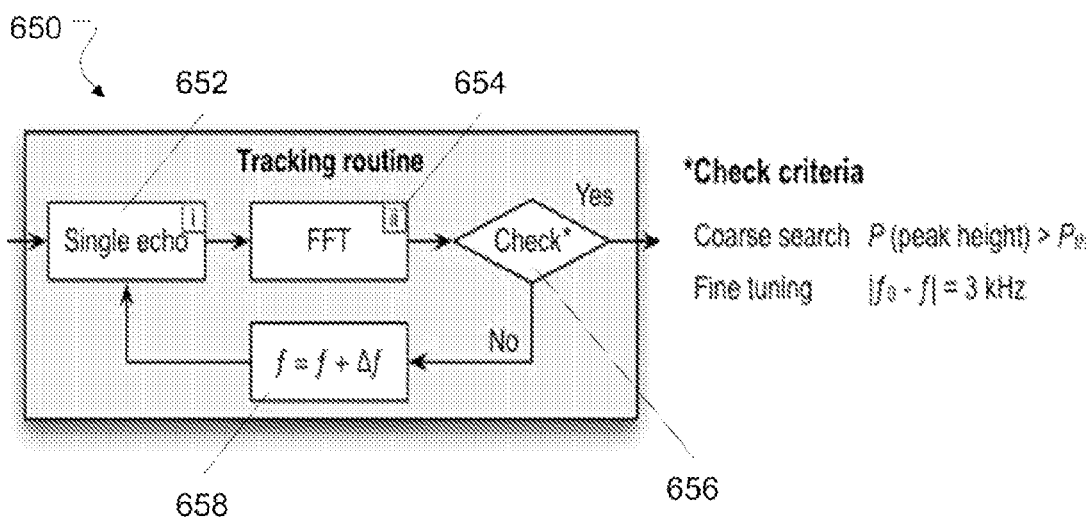
FIG. 6B is a flowchart describing a process implemented by a DMR system to perform a coarse search.
Figure 6C:
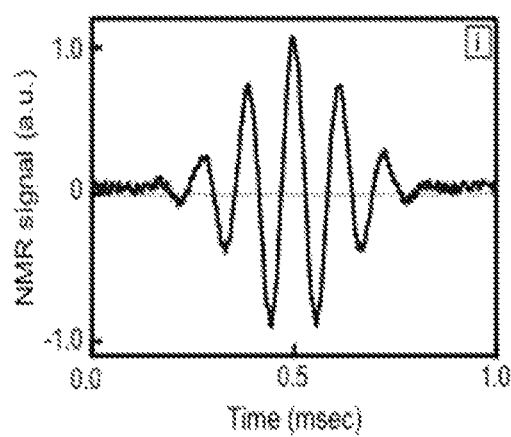
FIG. 6C is a graph showing a single measured NMR echo used for resonance tracking.

A flowchart 650 in FIG. 6B describes the process implemented by the DMR system 10 to perform a coarse search. In a first step (652), the sample is excited using an RF signal having the initial excitation frequency $f_i$ and an NMR spin echo is measured from the sample. FIG. 6C is a graph showing a single measured NMR echo used for resonance tracking. In a second step (654), the measured NMR signal is transformed into the frequency domain (e.g., using fast Fourier transformation). The spectral power (P) of the peak in the measured bandwidth (e.g., between 1-30 kHz) is then compared to a pre-defined threshold $P_{th}$ for reliable peak identification in a third step (656). If the measured spectral power P is less than the threshold power $P_{th}$, the coarse search continues by incrementing the excitation frequency f by an amount $\Delta f$ in a fourth step (658). In general, any suitable value for $\Delta f$ can be used including about 1 kHz, 2 kHz, 5 kHz, 10 kHz, 15 kHz, or 20 kHz. In general, these frequency is set to be on the same order as the bandwidth of the measurement, e.g., about 10 kHz. Otherwise, the Larmor frequency $f_0$ is identified as the frequency corresponding to the location of the peak spectral power and the tracking proceeds to a fine-tuning routine.

Figure 6D:
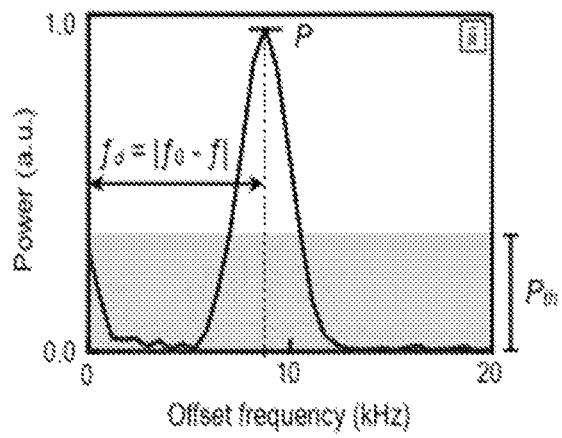
FIG. 6D is a graph showing the echo signal in the frequency domain indicating how P and $f_d$ are defined for coarse and fine-tuning, respectively.

Referring again to FIG. 6A, once the Larmor frequency $f_0$ is identified, the system 10 automatically fine-tunes the excitation frequency f in a third step (606). For fine-tuning, the frequency offset $f_d(=|f-f_0|)$ is measured in the FFT domain, and f is adjusted iteratively to reach a predetermined target offset (e.g., $f_d$=3 kHz). FIG. 6D is a graph showing the echo signal in the frequency domain indicating how P and $f_d$ are defined for coarse and fine-tuning, respectively. The target offset $f_d$ can be chosen to minimize the noise figure of amplifiers and hence maximize the overall signal-to-noise of the electronics. The target offset can be manually set by a user through the data processing device 50 or pre-set by the software to the optimal value for a given pre-amplifier and does not need to be changed during common use. Once the f and $f_0$ are determined, NMR measurements of the sample are performed to obtain the data for determining the longitudinal T1 and/or transverse T2 relaxation times using either inversion-recovery and/or CPMG pulse sequences, respectively in a fourth step (608). The relaxation times are calculated in a data processing step (610).

Figure 6E:
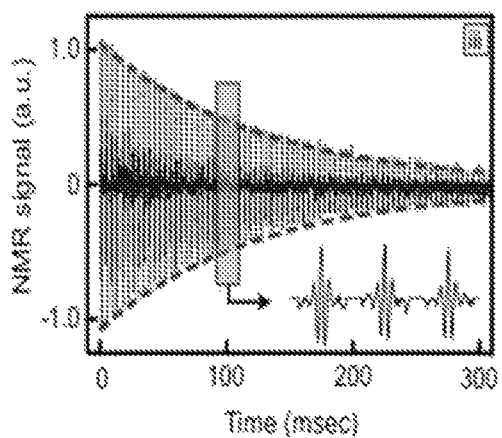
FIG. 6E is a graph showing an NMR signal obtained using CPMG pulse sequences with $f_d$=3 kHz.
Figure 6F:
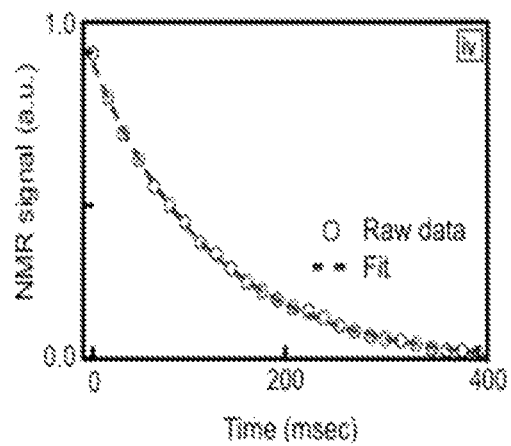
FIG. 6F is a graph showing the processed NMR signal used to obtain the transverse $T_2$ relaxation time.

FIG. 6E is a graph showing an NMR signal obtained using CPMG pulse sequences with $f_d$=3 kHz. FIG. 6F is a graph showing the processed NMR signal used to obtain the transverse $T_2$ relaxation time. For subsequent measurements, the tracking time can be minimized by using the Larmor frequency $f_0$ identified in the previous measurement as the starting value for the initial excitation frequency $f_i$ and by skipping a coarse search. In contrast to conventional NMR spectroscopy techniques, the automatic frequency tracking technique described above relies on keeping the frequency offset from the Larmor frequency constant as opposed to keeping the Larmor frequency itself constant.

Applications

The new DMR systems described herein can be used for diagnostic testing near a patient (so called "point-of-care" testing). For example, the DMR systems are portable and can be used in resource-limited and/or remote settings including, for example, in an ambulance, in an emergency room, in an intensive care unit, or in other patient settings for the rapid, quantitative, and multi-channeled detection of biological targets. Furthermore, the system simplifies use and data logging/sharing for medical personal through a mobile computing device interface. Examples of detection targets are discussed in more detail below and in the Examples section.

Detecting Infectious Agents

The DMR assay is a modular platform. By modifying the functional ligands on magnetic particles, the same DMR system can be used to measure many different biological targets, including small molecules, proteins, nucleic acids, pathogens, and cancer cells. The target analytes can be easily detected with the new system with minimal preparation steps (e.g., no need for intensive purification steps). The DMR system measurement is fast (e.g., less than 30 minutes) and simple compared to conventional detection methods (e.g., a culture-based method, a PCR-based method).

For example, the portable DMR system can be deployed for tuberculosis (TB) diagnosis. In "Reducing the Global Burden of Tuberculosis: The Contribution of Improved Diagnostics" (E. Keeler et al., Nature, 2006, 444, 49-57), it was projected that an inexpensive tool, which can rapidly detect MTB (Mycobacterium tuberculosis) with high sensitivity and specificity at the primary care level, could save more than 400,000 lives annually. The new DMR system, combined with highly magnetized nanoparticles and microfluidic-based filtration could be used as such a TB detection platform, offering sensitivity far superior to smear microscopy. Furthermore, using the new DMR, a diagnosis can be obtained immediately (less than 30 minutes), reducing delays in treatment and simplifying patient treatment. Additionally, the diagnosis can be easily stored and shared electronically, enabling medical decisions to be made remotely and for real-time tracking and mapping of the disease spread.

Rare Cell Detection

The new systems and methods can be used to detect rare cells, such as circulating tumor cells (CTC) in a blood sample or fetal cells in maternal blood samples. For example, primary tumor cells or circulating tumor cells can be targeted with magnetic particles and can be detected using the new DMR system for a rapid and comprehensive profiling of cancers. By changing binding molecules on the particle surface, different types of cells can be detected (e.g., circulating endothelial cells for heart disease). Thus, miniaturized NMR can be used as a powerful diagnostic and prognostic tool. The targeted and detected cells could be cancer cells, stem cells, immune cells, or other cells including, for example, circulating tumor cells (EpCAM) and circulating endothelial cells (CD146). In some implementations, the system sensitivity can detect as low as a few cells per microliter of detection volume, i.e., the device itself has the capacity for single-cell detection. The systems and methods also can be used to detect small molecules, proteins, nucleic acids, or pathogens.

Detection Assays

Figure 7:
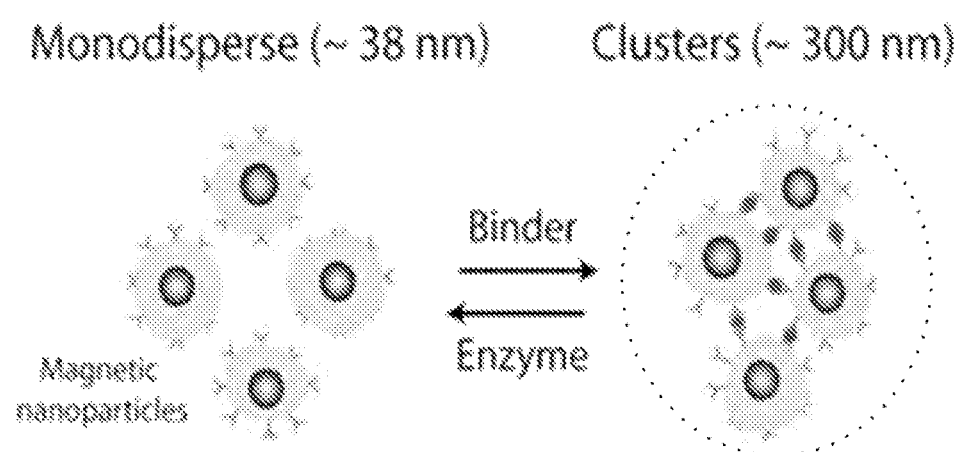
FIG. 7 is a schematic of monodisperse and clustered magnetic particles.

FIG. 7 illustrates the principle of proximity assay detection using magnetic nanoparticles. When monodisperse magnetic particles, which can range in size from 10 to 50 nm, e.g., 20 to 40, e.g., 38 nm, form clusters after binding to a target analyte, which have an overall diameter of at least 100 nm, e.g., 150, 200, 250, 300, 350, 400, 450, 500 nm, or larger. The self-assembled clusters become more efficient at dephasing nuclear spins of surrounding water protons, leading to the decrease of spin-spin relaxation time (T2). For example, in some embodiments, the proximity assay can be conducted to detect the presence of avidin in solution.

Multiplexed Detection

Detecting multiple biomarkers in one parent sample is an important and highly desirable task for diagnosis and prognosis of complex diseases. For example, there is no ubiquitous biomarker for cancer; multi-channeled screening is required to correctly identify tumor types. The DMR system offers a method to detect different relevant biomarkers from the aliquots of a single, parent sample, e.g. in patients with cancer or metabolic disorders. The DMR system is well suited for this application because many sensors (e.g., microcoils) can be accommodated on a small area as an array format, and only a small volume of a sample is consumed per measurement. Examples of tumor cell biomarkers that can be detected include MUC-1, EGFR, B7-H3, Her2, Ki-67, EpCam, Vim, CK18, and p53. In some embodiments, the devices described herein are used to detect at least four biomarkers: MUC1, EGFR, EpCAM, and HER2, in a sample, and diagnosing the presence of tumor cells in the sample based on the presence and/or level of the four biomarkers. See U.S. Provisional patent application entitled "Molecular Analysis of Tumor Samples" and assigned 61/515,150, filed concurrently herewith.

EXAMPLES

The invention is further described in the following examples, which do not limit the scope of the invention described in the claims.

Example 1: Evaluation of DMR Temperature Variation Compensation

The DMR system was evaluated for its ability to compensate for temperature variations. A sample was prepared by adding magnetic nanoparticles (cross-linked iron oxide particles aminated to provide primary amine groups ($CLIO-NH_2$)) into a phosphine buffer saline (PBS) solution. In particular, CLIO particles having ferrite cores (about 7 nm in diameter) were covered with a layer of 10 kDa dextran. The dextran layer was cross-linked with epichlorohydrin to stabilize the coating, and subsequently aminated to provide primary amine groups ($CLIO-NH_2$). The hydrodynamic diameter of CLIO, measured by dynamic light scattering (Zetasizer 1000HS; Malvern Instruments), was 38 nm.

The sample was added to a sample tube and then loaded into the DMR system. The following CPMG pulse sequences were used for T2 measurements. For short T2

(<300 ms), the number of pulses were set equal to 400, the pulse width was set equal to 50 μs, the TE (echo time-time between pulses) was 2.5 ms, the TR (repetition time-wait time before the spin echo routine is repeated) was 1 s, and the number of averages was 10. For long T2 (>300 ms), the number of pulses was set equal to 500, the pulse width was set equal to 50 μs, the TE was 4 ms, the TR was 5 s, and the number of averages was 10. For the T1 measurements, the following inversion recovery parameters were used: number of spin inversion-recovery data points was 200, the pulse width was set equal to 50 μs and the number of averages/spin inversion recovery was 10. The external magnetic field applied by the permanent magnet was about 0.47 T.

Figure 8:
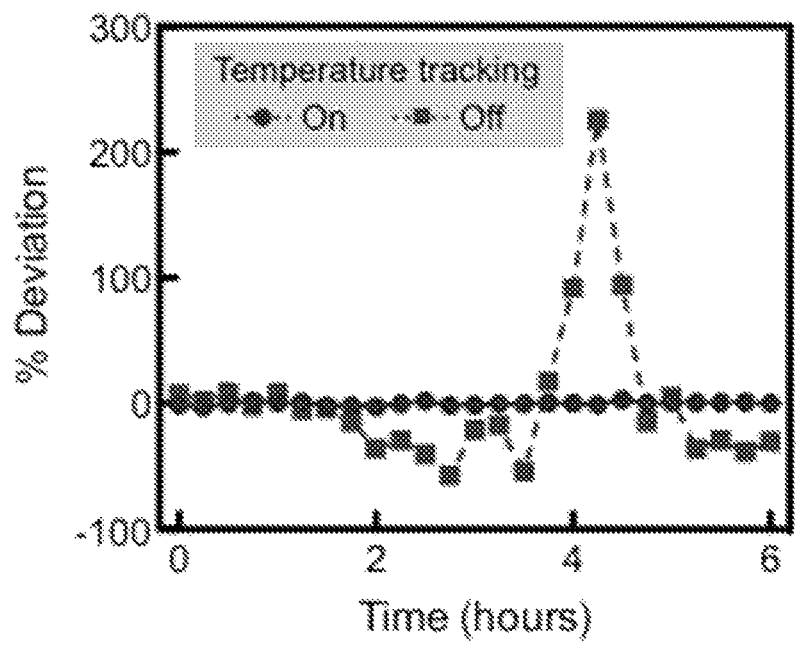
FIG. 8 is a graph showing a comparative example in which a transverse relaxation time (T2) of a sample was measured with and without temperature compensation.

FIG. 8 is a graph showing a comparative example in which the transverse relaxation time $T_2$ of the same sample was measured with and without temperature compensation. An initial starting value of about 100 ms was obtained for $T_2$. When the Larmor frequency $f_0$ was allowed to drift due to typical fluctuations in room temperature (ΔT of approximately 2° C.), but the RF excitation frequency f for the sample excitation was fixed, the $T_2$ values varied up to 200% relative to the starting value for $T_2$. However, when $|f_0-f|$ was held constant (3 kHz) by tracking $f_0$ and adjusting f, the $T_2$ variations were significantly reduced to less than 1%. These results illustrate the importance of keeping a constant frequency offset ($|f_0-f|$) for robust, reliable DMR measurements. For a typical DMR measurement in clinical conditions, temperature tracking allows a more robust and reliable measurement of $T_2$, with an average error of about 1% compared to about 50% without temperature tracking.

Figure 9:
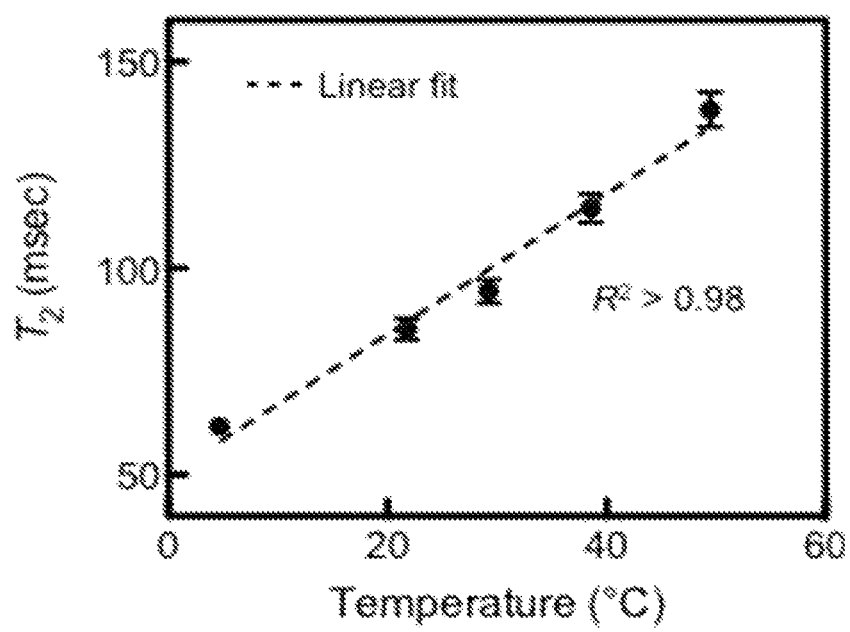
FIG. 9 is a graph that shows the transverse relaxation time (T2) values of a sample measured at different environmental temperatures.

The new DMR system was then tested in environmental settings with a wide range of temperature differences (between about 4-50° C.). To determine the measurement accuracy, the linear dependence of $T_2$ on temperature was utilized. FIG. 9 is a graph that shows the $T_2$ values of a sample measured at different environmental temperatures. For a given environment setting, the DMR system was operated with the temperature tracking on, to compensate for minute temperature variations (about 1° C.). The results show a linear relationship (total square error $R_e^2 > 98\%$) as theoretically predicted, demonstrating reliable measurements over a wide range of temperatures. These results indicate that the portable DMR can be utilized for robust diagnostics in various settings: medical clinics in both the developed and developing world, military settings, and in the field by emergency medical first responders.

Example 2: Benchmarking the DMR System

Figure 10:
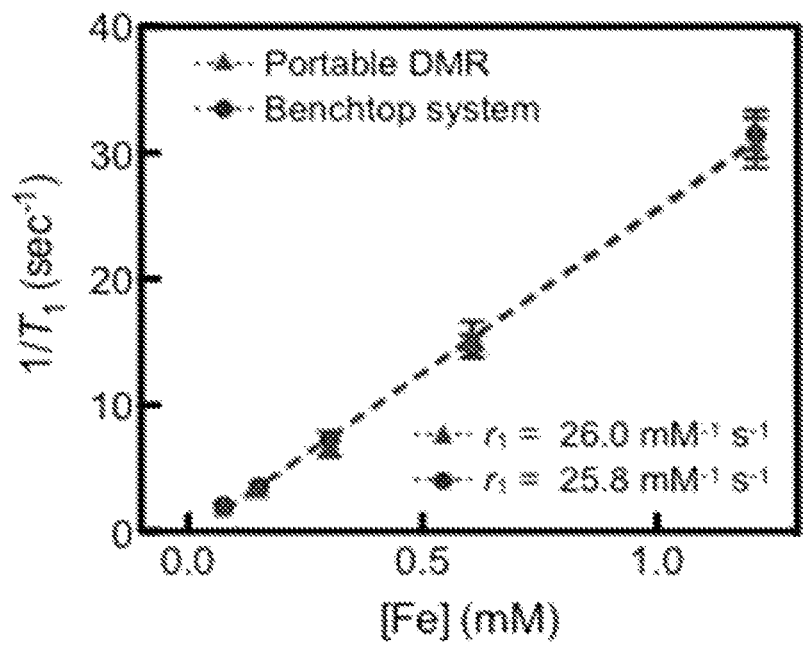
FIG. 10 is a graph showing measured longitudinal relaxation rate against metal concentration.
Figure 11:
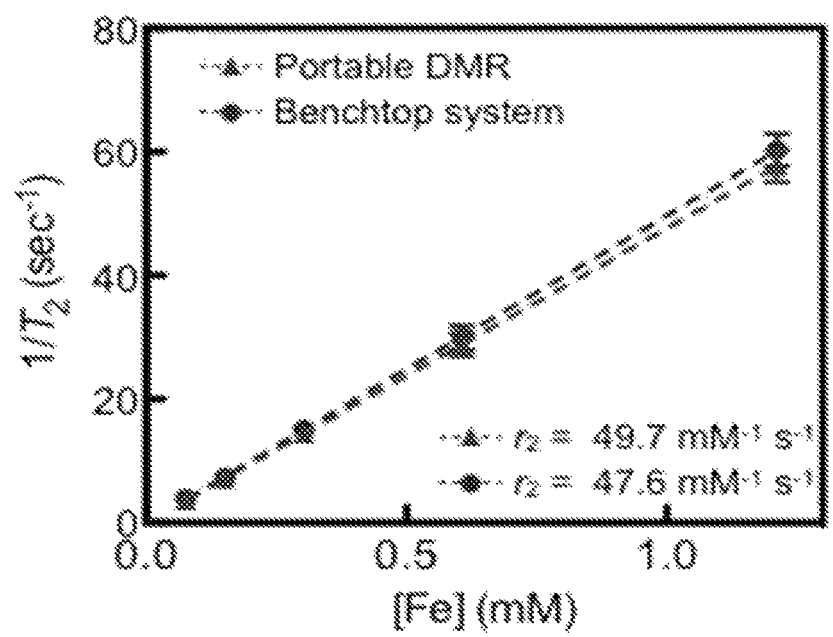
FIG. 11 is a graph showing measured transverse relaxation rate against metal concentration.

The performance of the new DMR system was compared to the performance of a large benchtop NMR relaxometer to verify the accuracy of the system. The benchtop NMR relaxometer (Minispec mq20 from Bruker) operates at a similar external magnetic field of 0.47 T to the new DMR system. Samples with varying amounts of CLIO were prepared as discussed in Example 1. The magnetic nanoparticles' longitudinal $T_1$ and transverse $T_2$ relaxation times were measured using the inverse recovery and CPMG pulse sequences, respectively using the same pulse sequence parameters described above in Example 1. Once relaxation times were recorded, the longitudinal $r_1$ and $r_2$ relaxation rates were calculated, where the relaxation rates are the capacities of the magnetic particles to induce changes in $T_1$ and $T_2$ and are equal to the inverse of the corresponding relaxation time. FIGS. 10 and 11 are graphs showing the measured longitudinal and transverse relaxation rates against metal concentrations, respectively. The measured $r_1$ and $r_2$ showed excellent agreement (P<0.4) between the portable DMR and the benchtop system, reporting statistically the same values. These results indicate that, the portable DMR system exhibits similar performance to the benchtop equipment while using much smaller volumes of samples (2 μl vs. 300 μl), and operating without a bulky, heated container for temperature control.

Example 3: Avidin Detection

To demonstrate biological application of the new DMR system for rapid and sensitive diagnosis of small molecule disease markers, avidin-biotin interactions were characterized. To detect avidin, we used biotinylated CLIO (CLIO-biotin). To render CLIO target specific, the particle surface was modified with affinity ligands. To biotinylate CLIO—NH$_2$, 2 mg sulfosuccinimidyl-6-(biotinamido)hexanoate (sulfo-NHS-LC-biotin) was mixed with 0.5 mg CLIO in 1.25 ml PBS solution (pH 7.2) for 3 hours at room temperature. The biotinylated CLIO was purified using membrane filtration (Amicon Mw 30000; Millipore) and with Sephadex G-50 (GE Healthcare) using PBS (pH 7.2) as the eluent buffer. Using a stock concentration of 1 mg ml$^{-1}$ [Av](ImmunoPure Avidin; Pierce Biotechnology) in PBS, dilutions were created spanning logarithmically from 800 nM [Av] to 2 nM [Av]. These samples were incubated with 0.2 mM [Fe] CLIO-biotin. Following 30 minute incubation at room temperature, DMR measurements were performed on 2 μl samples with temperature tracking on. The magnetic nanoparticles' longitudinal $T_1$ and transverse $T_2$ relaxation times were measured using the same inverse recovery and CPMG pulse sequence parameters, described above in Example 1.

Figure 12:
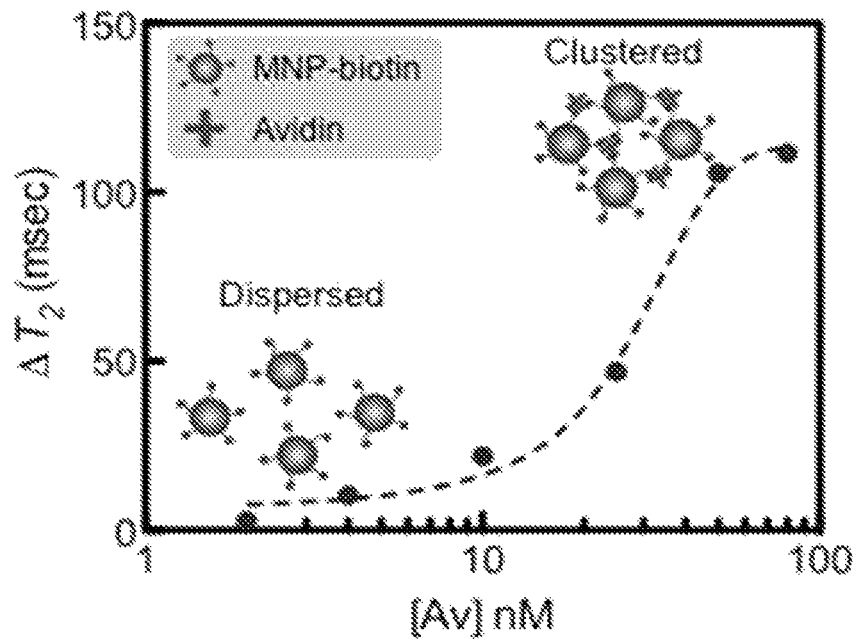
FIG. 12 is a graph showing measured change in transverse relaxation time T2 versus avidin concentration.

For target sensing (e.g., protein in solution), the DMR assay utilizes the phenomenon of magnetic relaxation switching, in which MNPs are cross-linked with target molecules to form nanometer-scale clusters. The increasing amount of avidin added to the solutions led to the formation of bigger particle clusters. FIG. 12 is a graph that shows transverse relaxation time $T_2$ versus avidin concentration. As shown in the graph, the $T_2$ values of samples showed a dependence on the avidin-dose concentration. The detection limit was approximately 140 pg (2 fmol of avidin) or 1 nM. These results indicate that the new DMR system can be used to detect molecular targets.

Example 4: Bacterial Detection

To demonstrate biological application of the new DMR system for rapid and sensitive diagnosis of large disease markers, bacterial targets were labeled with magnetic nanoparticles. For bacterial targeting, CLIO was conjugated with vancomycin, an antibiotic that recognizes D-alanyl-D-alanine moieties in the bacterial cell wall. CLIO (2 mg Fe) was first mixed with 0.17 mg succinic anhydride in PBS (pH 8) for 3 hours to convert the amine groups into carboxylate groups. The succinylated CLIO was then activated with 2 mg EDC (1-ethyl-3-(3-dimethylaminopropyl)carbodiimide) and 2 mg sulfo-NHS (N-hydroxysulfosuccinimide) in MES buffer solution (pH 6) for 60 minutes, and purified using a membrane filter and Sephadex G-50 in PBS. The activated CLIO conjugates were mixed with 7.4 mg vancomycin in PBS (pH 7.2) for 2 hours. The CLIO-vancomycin conjugates were then purified using a membrane filter and Sephadex G-100 in PBS.

*Staphylococcus aureus* (see FIG. 13 inset) was used as a model target for bacterial detection. Bacterial specimen was purchased (strain #25923; ATCC) and cultured in vendor recommended media (m *Staphylococcus* broth; BD). The density of bacteria was estimated by measuring the optical density (OD) at 600 nm using an ultraviolet-visible spectrometer (Cary 50 UV-Vis Spectrophotometer, Varian Inc.). Beginning with a bacteria concentration of $5 \times 10^5$ colony forming units (CFU) $ml^{-1}$, serial dilutions were created spanning logarithmically from $5 \times 10^5$ CFU $ml^{-1}$ to $10^3$ CFU $ml^{-1}$. These samples were incubated for about 15 minutes at 20° C. with 0.2 mM [Fe] vancomycin conjugated CLIO. Following the incubation, the excess CLIO was removed via centrifugation (2000 g), and the samples were re-suspended in PBS. Control samples were prepared by incubating samples with non-modified CLIO.

Figure 13:
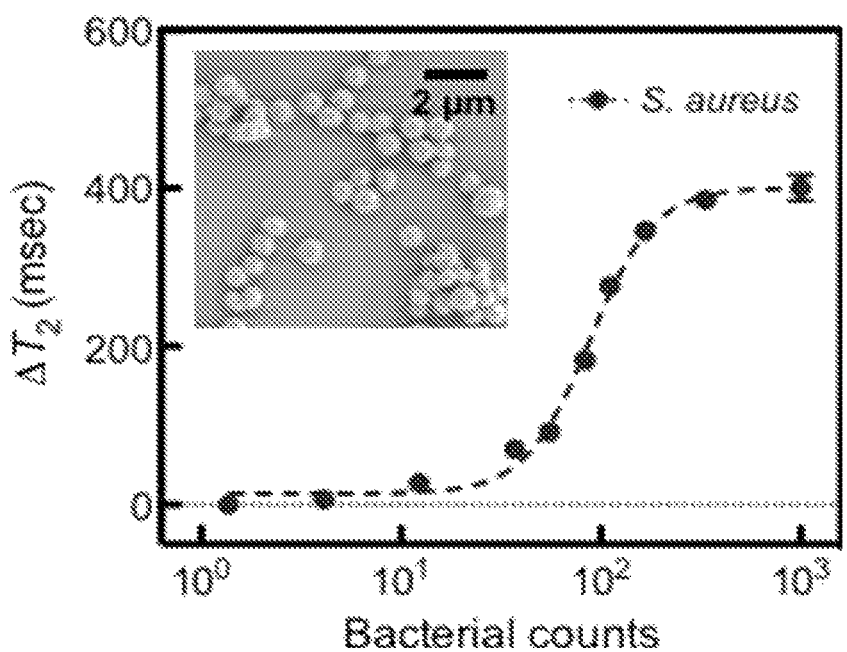
FIG. 13 is a graph showing the change in relaxation time T2 versus bacterial counts of *Staphylococcus aureus*. An image of the bacteria *Staphylococcus aureus* is shown in the inset.

DMR measurements were performed on 2 µl samples with temperature tracking on. Unbound particles were removed prior to measurements. The magnetic nanoparticles' longitudinal $T_1$ and transverse $T_2$ relaxation times were measured using the same inverse recovery and CPMG pulse sequence parameters, described above in Example 1. The measured $T_2$ changes ($\Delta T_2$) were bacterial concentration dependent, and the portable DMR could reliably detect as few as about 10 bacteria in a 2 µl sample volume. FIG. 13 is a graph that shows the change in relaxation time $T_2$ versus bacterial counts. The detection limit was about 10 CFU in a 2 µl detection volume. These results indicate that the DMR measurements of pathogens can be simpler and faster (30 minutes) than conventional cultivation or biochemical methods, such as culturing in a petri dish or polymerase chain reaction (PCR) based detection.

Other Embodiments

It is to be understood that while the invention has been described, the foregoing description is intended to illustrate and not to limit the scope of the invention, which is defined by the scope of the appended claims. Other aspects, advantages, and modifications are within the scope of the following claims.

What is claimed is:

1. A portable magnetic resonance system comprising:
   a permanent magnet;
   a nuclear magnetic resonance probe; and
   control electronics configured to:
      transmit to the probe a magnetic resonance excitation signal having an excitation frequency f,
      receive from the probe a magnetic resonance measurement signal;
      detect in the magnetic resonance measurement signal a magnetic resonance frequency $f_0$; and
      automatically adjust the excitation frequency f until the difference between the excitation frequency and the magnetic resonance frequency is approximately equal to a predetermined offset,
   wherein the control electronics are further configured to measure at least one of a sample longitudinal relaxation time $T_1$ and a sample transverse relaxation time $T_2$ from the magnetic resonance measurement signal when the difference between the excitation frequency and the magnetic resonance frequency is approximately equal to the predetermined offset.

2. The magnetic resonance diagnostic system of claim 1, wherein the control electronics are configured to detect the magnetic resonance frequency $f_0$ based on a spectral power of the magnetic resonance measurement signal.

3. The magnetic resonance diagnostic system of claim 1, wherein the nuclear magnetic resonance probe comprises an encapsulating block and a microcoil embedded within the encapsulating block.

4. The magnetic resonance diagnostic system of claim 3, wherein the encapsulating block comprises polydimethylsiloxane (PDMS).

5. The magnetic resonance diagnostic system of claim 3, wherein the encapsulating block comprises a bore for receiving a sample container.

6. The magnetic resonance diagnostic system of claim 5, wherein the microcoil surrounds the bore.

7. The magnetic resonance diagnostic system of claim 1, wherein the permanent magnet comprises an opening configured to receive the nuclear magnetic resonance probe.

8. The magnetic resonance diagnostic system of claim 1, wherein the opening extends from a first side of the magnet through the magnet center to a second opposite side of the magnet.

9. The magnetic resonance diagnostic system of claim 1, further comprising a microfluidic network configured to contain a sample fluid.

10. The magnetic resonance diagnostic system of claim 1, further comprising a portable data processing device to communicate with the control electronics, wherein the portable data processing device is operable to:
    transmit one or more commands to the control electronics to initiate measurement of at least one of a sample longitudinal relaxation time $T_1$ or a sample transverse relaxation time $T_2$;
    receive from the control electronics data corresponding to the sample longitudinal relaxation time $T_1$ or the sample transverse relaxation time $T_2$, or both; and
    output the data to a display.

11. A portable magnetic resonance system comprising:
    a nuclear magnetic resonance probe comprising a microcoil assembly and a sample receiving area, wherein the microcoil assembly surrounds the sample receiving area; and
    control electronics configured to:
       transmit to the probe a magnetic resonance excitation signal having an excitation frequency f,
       receive from the probe a magnetic resonance measurement signal;
       detect in the magnetic resonance measurement signal a magnetic resonance frequency $f_0$; and
       automatically adjust the excitation frequency f until the difference between the excitation frequency and the magnetic resonance frequency is approximately equal to a predetermined offset.

12. The portable magnetic resonance system of claim 11, further comprising a magnet having an opening, wherein the nuclear magnetic resonance probe is positioned within the opening in the magnet.

* * * * *

UNITED STATES PATENT AND TRADEMARK OFFICE
CERTIFICATE OF CORRECTION

PATENT NO. : 9,874,564 B2
APPLICATION NO. : 14/006389
DATED : January 23, 2018
INVENTOR(S) : Ralph Weissleder, Hakho Lee and David Issadore It is certified that error appears in the above-identified patent and that said Letters Patent is hereby corrected as shown below:

In the Claims

Column 19, Claim 1, Line 46:
Delete "f," and insert --f;--

Column 20, Claim 11, Line 47:
Delete "f," and insert --f;--

Signed and Sealed this
Third Day of April, 2018

Andrei Iancu
*Director of the United States Patent and Trademark Office*